(12) United States Patent
Monville et al.

(10) Patent No.: US 12,618,045 B2
(45) Date of Patent: May 5, 2026

(54) AUTOMATED METHOD FOR PREPARING RETINAL PIGMENT EPITHELIUM CELLS

(71) Applicant: CENTRE D'ETUDE DES CELLULES SOUCHES (CECS), Corbeil-Essonnes (FR)

(72) Inventors: Christelle Monville, Champigny sur Marne (FR); Florian Regent, Le Hezo (FR); Lise Morizur, Pontault-Combault (FR); Karim Ben M'Barek, Creteil (FR)

(73) Assignee: CENTRE D'ETUDE DES CELLULES SOUCHES (CECS), Corbeil-Essonnes (FR)

( * ) Notice: Subject to any disclaimer, the term of this patent is extended or adjusted under 35 U.S.C. 154(b) by 861 days.

(21) Appl. No.: 17/621,068

(22) PCT Filed: Jun. 19, 2020

(86) PCT No.: PCT/EP2020/067177
§ 371 (c)(1),
(2) Date: Dec. 20, 2021

(87) PCT Pub. No.: WO2020/254623
PCT Pub. Date: Dec. 24, 2020

(65) Prior Publication Data
US 2022/0333065 A1 Oct. 20, 2022

(30) Foreign Application Priority Data
Jun. 21, 2019 (EP) .................................... 19305807

(51) Int. Cl.
*C12N 5/0793* (2010.01)
*A61P 27/00* (2006.01)

(52) U.S. Cl.
CPC .............. *C12N 5/062* (2013.01); *A61P 27/00* (2018.01); *C12N 2501/15* (2013.01); *C12N 2501/155* (2013.01); *C12N 2506/45* (2013.01)

(58) Field of Classification Search
None
See application file for complete search history.

(56) References Cited

U.S. PATENT DOCUMENTS 8,956,866 B2 * 2/2015 Idelson ................ C12N 5/0621
435/387

FOREIGN PATENT DOCUMENTS

| | | |
|---|---|---|
| JP | 2018521677 A | 8/2018 |
| WO | 2008107695 A1 | 9/2008 |
| WO | 2017021972 A1 | 2/2017 |

OTHER PUBLICATIONS

Crombie DE, Daniszewski M, et al. Development of a Modular Automated System for Maintenance and Differentiation of Adherent Human Pluripotent Stem Cells. SLAS Discov. Sep. 2017;22(8):1016-1025. doi: 10.1177/2472555217696797. Epub Mar. 13, 2017. PMID: 28287872. (Year: 2017).*

(Continued)

*Primary Examiner* — Evelyn Y Pyla
*Assistant Examiner* — Jagamya Vijayaraghavan
(74) *Attorney, Agent, or Firm* — NIXON & VANDERHYE

(57) ABSTRACT

Disclosed are methods for preparing retinal pigment epithelium (RPE) cells from pluripotent stem cells (PSCs). More particularly, it represents an automated method that combines in a sequential manner three differentiating agents to direct the differentiation of human PSCs into RPE cells.

14 Claims, 7 Drawing Sheets

Specification includes a Sequence Listing.

(56)                    References Cited

OTHER PUBLICATIONS

Foltz LP, Clegg DO. Rapid, Directed Differentiation of Retinal Pigment Epithelial Cells from Human Embryonic or Induced Pluripotent Stem Cells. J Vis Exp. Oct. 30, 2017;(128):56274. doi: 10.3791/56274. PMID: 29155780; PMCID: PMC5755280. (Year: 2017).*

Kokkinaki M, et al. Human induced pluripotent stem-derived retinal pigment epithelium (RPE) cells exhibit ion transport, membrane potential, polarized vascular endothelial growth factor secretion, and gene expression pattern similar to native RPE. Stem Cells. May 2011;29(5):825-35. (Year: 2011).*

Leach LL, Buchholz DE, Nadar VP, Lowenstein SE, Clegg DO. Canonical/β-catenin Wnt pathway activation improves retinal pigmented epithelium derivation from human embryonic stem cells. Invest Ophthalmol Vis Sci. Jan. 20, 2015;56(2):1002-13. doi: 10.1167/iovs.14-15835. PMID: 25604686. (Year: 2015).*

Dulbecco's Modified Eagle Medium (DMEM). https://www.sigmaaldrich.com/us/en/products/cell-culture-and-analysis/cell-culture-media-and-buffers/classical-media-and-buffers/dulbeccos-modified-eagle-medium?srsltid=AfmBOooSm14OGIXtgRbMZIMRjGWRovO-3xJMLPcHpdGzyNLdsd1jYlly. retrieved Jan. 31, 2025 (Year: 2025).*

Alberts B, Johnson A, Lewis J, et al. Molecular Biology of the Cell. 4th edition. New York: Garland Science; 2002. Isolating Cells and Growing Them in Culture. Available from: https://www.ncbi.nlm.nih.gov/books/NBK26851/ (Year: 2002).*

Suzuki, K., Koyanagi-Aoi, M., Uehara, K. et al. Directed differentiation of human induced pluripotent stem cells into mature stratified bladder urothelium. Sci Rep 9, 10506 (2019). https://doi.org/10.1038/s41598-019-46848-8 (Year: 2019).*

Yoda K, et al Optimization of the treatment conditions with glycogen synthase kinase-3 inhibitor towards enhancing the proliferation of human induced pluripotent stem cells while maintaining an undifferentiated state under feeder-free conditions. J Biosci Bioeng. Mar. 2019;127(3):381-387. (Year: 2019).*

International Search Report for PCT/EP2020/067177, mailed Sep. 15, 2020, 5 pages.

Written Opinion of the ISA for PCT/EP2020/067177, mailed Sep. 15, 2020, 10 pages.

Search Report for EP19305807, Dec. 11, 2019, 4 pages.

Achberger Kevin et al., "Stem cell-based 1-15 retina models", Advanced Drug Delivery Reviews, vol. 140, May 17, 2018, pp. 33-50.

Erino Matsumoto et al, "Fabricating retinal pigment epithelial cell sheets derived from human induced pluripotent stem cells in an automated closed culture system for regenerative medicine", PLOS ONE, vol. 14, No. 3, Mar. 13, 2019, p. e0212369.

Mee-Hae Kim et al., "Development of an automated chip culture system with integrated on-line monitoring for maturation culture of retinal pigment epithelial cells", Aims Bioengineering, vol. 4, No. 4, Oct. 18, 2017, pp. 402-417.

Thomas Rob J et al., "Automated, scalable culture of human embryonic stem cells in feeder-free conditions", Biotechnology and Bioengineering, vol. 102, No. 6, Apr. 15, 2009, pp. 1636-1644.

Maria Idelson et al., "Directed Differentiation of Human Embryonic Stem Cells into Functional Retinal Pigment Epithelium Cells", Cell Stem Cell, vol. 5, No. 4, Oct. 1, 2009, pp. 396-408.

Karim Ben M'Barek et al., "Cell Therapy for Retinal Dystrophies: From Cell Suspension Formulation to Complex Retinal Tissue Bioengineering", Stem Cells International, vol. 2019, Jan. 23, 2019 (Jan. 23, 2019), pp. 1-14.

Florian Regent et al., "Automation of human pluripotent stem cell differentiation toward retinal pigment epithelial cells for large-scale productions", Scientific Reports, vol. 9, No. 1, Jul. 23, 2019.

* cited by examiner

B.

□ RPE spontaneous differentiation
  with manual enrichment

■ RPE automated differentiation

C.

SEQUENCE LISTING

```
<160> NUMBER OF SEQ ID NOS: 26

<210> SEQ ID NO 1
<211> LENGTH: 20
<212> TYPE: DNA
<213> ORGANISM: Artificial Sequence
<220> FEATURE:
<223> OTHER INFORMATION: 18S FWR primer

<400> SEQUENCE: 1
gaggatgagg tggaacgtgt                                            20

<210> SEQ ID NO 2
<211> LENGTH: 20
<212> TYPE: DNA
<213> ORGANISM: Artificial Sequence
<220> FEATURE:
<223> OTHER INFORMATION: 18S REV primer

<400> SEQUENCE: 2
tcttcagtcg ctccaggtct                                            20

<210> SEQ ID NO 3
<211> LENGTH: 20
<212> TYPE: DNA
<213> ORGANISM: Artificial Sequence
<220> FEATURE:
<223> OTHER INFORMATION: NANOG FRW primer

<400> SEQUENCE: 3
caaaggcaaa caacccactt                                            20
```

-continued

```
<210> SEQ ID NO 4
<211> LENGTH: 20
<212> TYPE: DNA
<213> ORGANISM: Artificial Sequence
<220> FEATURE:
<223> OTHER INFORMATION: NANOG REV primer

<400> SEQUENCE: 4
tctgctggag gctgaggtat                                                     20

<210> SEQ ID NO 5
<211> LENGTH: 21
<212> TYPE: DNA
<213> ORGANISM: Artificial Sequence
<220> FEATURE:
<223> OTHER INFORMATION: RAX FRW primer

<400> SEQUENCE: 5
ggcaaggtca acctaccaga g                                                   21

<210> SEQ ID NO 6
<211> LENGTH: 21
<212> TYPE: DNA
<213> ORGANISM: Artificial Sequence
<220> FEATURE:
<223> OTHER INFORMATION: RAX REV primer

<400> SEQUENCE: 6
catggaggac acttccagct t                                                   21

<210> SEQ ID NO 7
<211> LENGTH: 20
<212> TYPE: DNA
<213> ORGANISM: Artificial Sequence
<220> FEATURE:
<223> OTHER INFORMATION: SIX3 FRW primer

<400> SEQUENCE: 7
cctcccactt cttgttgcca                                                     20

<210> SEQ ID NO 8
<211> LENGTH: 21
<212> TYPE: DNA
<213> ORGANISM: Artificial Sequence
<220> FEATURE:
<223> OTHER INFORMATION: SIX3 REV primer

<400> SEQUENCE: 8
cgctactcgc cagaagtatg g                                                   21

<210> SEQ ID NO 9
<211> LENGTH: 20
<212> TYPE: DNA
<213> ORGANISM: Artificial Sequence
<220> FEATURE:
<223> OTHER INFORMATION: PAX6 FRW primer

<400> SEQUENCE: 9
gccagcaaca cacctagtca                                                     20

<210> SEQ ID NO 10
<211> LENGTH: 20
<212> TYPE: DNA
<213> ORGANISM: Artificial Sequence
<220> FEATURE:
```

-continued

<223> OTHER INFORMATION: PAX6 REV primer

<400> SEQUENCE: 10
tgtgagggct gtgtctgttc                                               20

<210> SEQ ID NO 11
<211> LENGTH: 20
<212> TYPE: DNA
<213> ORGANISM: Artificial Sequence
<220> FEATURE:
<223> OTHER INFORMATION: VSX2 FRW primer

<400> SEQUENCE: 11
ctgccggaag acaggataca                                               20

<210> SEQ ID NO 12
<211> LENGTH: 19
<212> TYPE: DNA
<213> ORGANISM: Artificial Sequence
<220> FEATURE:
<223> OTHER INFORMATION: VSX2 REV primer

<400> SEQUENCE: 12
tagagcccat actccgcca                                                19

<210> SEQ ID NO 13
<211> LENGTH: 20
<212> TYPE: DNA
<213> ORGANISM: Artificial Sequence
<220> FEATURE:
<223> OTHER INFORMATION: MITF FRW primer

<400> SEQUENCE: 13
ccgggtgcag aattgtaact                                               20

<210> SEQ ID NO 14
<211> LENGTH: 20
<212> TYPE: DNA
<213> ORGANISM: Artificial Sequence
<220> FEATURE:
<223> OTHER INFORMATION: MITF REV primer

<400> SEQUENCE: 14
ggacaatttt ggcattttgg                                               20

<210> SEQ ID NO 15
<211> LENGTH: 20
<212> TYPE: DNA
<213> ORGANISM: Artificial Sequence
<220> FEATURE:
<223> OTHER INFORMATION: RPE65 FRW primer

<400> SEQUENCE: 15
agcactgagt tgagcaagca                                               20

<210> SEQ ID NO 16
<211> LENGTH: 20
<212> TYPE: DNA
<213> ORGANISM: Artificial Sequence
<220> FEATURE:
<223> OTHER INFORMATION: RPE65 REV primer

<400> SEQUENCE: 16
ggcctgtctc acagaggaag                                               20

-continued

<210> SEQ ID NO 17
<211> LENGTH: 20
<212> TYPE: DNA
<213> ORGANISM: Artificial Sequence
<220> FEATURE:
<223> OTHER INFORMATION: CRALBP FRW primer

<400> SEQUENCE: 17
cacgctgccc aagtatgatg                                                                   20

<210> SEQ ID NO 18
<211> LENGTH: 20
<212> TYPE: DNA
<213> ORGANISM: Artificial Sequence
<220> FEATURE:
<223> OTHER INFORMATION: CRALBP REV primer

<400> SEQUENCE: 18
ccaggacagt tgaggagagg                                                                   20

<210> SEQ ID NO 19
<211> LENGTH: 22
<212> TYPE: DNA
<213> ORGANISM: Artificial Sequence
<220> FEATURE:
<223> OTHER INFORMATION: TYROSYNASE FRW primer

<400> SEQUENCE: 19
gtgtagcctt cttccaactc ag                                                                22

<210> SEQ ID NO 20
<211> LENGTH: 24
<212> TYPE: DNA
<213> ORGANISM: Artificial Sequence
<220> FEATURE:
<223> OTHER INFORMATION: TYROSYNASE REV primer

<400> SEQUENCE: 20
gttcctcatt accaaatagc atcc                                                              24

<210> SEQ ID NO 21
<211> LENGTH: 20
<212> TYPE: DNA
<213> ORGANISM: Artificial Sequence
<220> FEATURE:
<223> OTHER INFORMATION: BEST1 FRW primer

<400> SEQUENCE: 21
gtcagaggct cctccttcct                                                                   20

<210> SEQ ID NO 22
<211> LENGTH: 20
<212> TYPE: DNA
<213> ORGANISM: Artificial Sequence
<220> FEATURE:
<223> OTHER INFORMATION: BEST1 REV primer

<400> SEQUENCE: 22
tctgctccac cagtgttctg                                                                   20

<210> SEQ ID NO 23
<211> LENGTH: 23
<212> TYPE: DNA
<213> ORGANISM: Artificial Sequence
<220> FEATURE:
<223> OTHER INFORMATION: LUM FRW primer -continued

```
<400> SEQUENCE: 23
cttcaatcag atagccagac tgc                                              23

<210> SEQ ID NO 24
<211> LENGTH: 23
<212> TYPE: DNA
<213> ORGANISM: Artificial Sequence
<220> FEATURE:
<223> OTHER INFORMATION: LUM REV primer

<400> SEQUENCE: 24
agccagttcg ttgtgagata aac                                              23

<210> SEQ ID NO 25
<211> LENGTH: 25
<212> TYPE: DNA
<213> ORGANISM: Artificial Sequence
<220> FEATURE:
<223> OTHER INFORMATION: FN1 FRW primer

<400> SEQUENCE: 25
ggaaagtgtc cctatctctg atacc                                            25

<210> SEQ ID NO 26
<211> LENGTH: 20
<212> TYPE: DNA
<213> ORGANISM: Artificial Sequence
<220> FEATURE:
<223> OTHER INFORMATION: FN1 REV primer

<400> SEQUENCE: 26
aatgttggtg aatcgcaggt                                                  20
```

AUTOMATED METHOD FOR PREPARING RETINAL PIGMENT EPITHELIUM CELLS

This application is the U.S. national phase of International Application No. PCT/EP2020/067177 filed 19 Jun. 2020, which designated the U.S. and claims priority to EP patent application Ser. No. 19/305,807.0 filed 21 Jun. 2019, the entire contents of each of which are hereby incorporated by reference.

FIELD OF THE INVENTION

The present invention relates to methods for preparing retinal pigment epithelium (RPE) cells from pluripotent stem cells (PSCs). More particularly, the present invention relates to an automated method that combines in a sequential manner three differentiating agents to direct the differentiation of human PSCs into RPE cells.

BACKGROUND OF THE INVENTION

The retinal pigment epithelium (RPE) is a monolayer of pigmented cells localized between the neuroretina and the choroids.

The RPE cells play roles in the maintenance and function of the retina and its photoreceptors. These include the formation of the blood-retinal barrier, absorption of light and protection against photooxidation, transport of nutrients to the neural retina, regeneration of visual pigment, and phagocytosis of shed photoreceptor membranes.

Human pluripotent stem cells (hPSCs), including human embryonic stem cells (hESCs) and human induced pluripotent stem cells (hiPSCs) are characterized by unlimited self-renewal and their ability to differentiate into any cell type. Due to these properties, extensive efforts have been done to use them as a source material for cell therapy to repair damaged tissues. At the forefront of cell therapy, the replacement of the retinal pigment epithelium, acts as a proof of concept. RPE cells play crucial roles in sight and their dysfunction or their loss may engender the secondary loss of photoreceptors. RPE cells are altered in 5-6% of Retinitis Pigmentosa cases and in Age-related Macular Degeneration (AMD). AMD is the leading cause of blindness in developed countries with more than 150 million people affected worldwide, a figure that will increase in the coming years. It can be classified into two groups, dry (atrophic) or wet (exudative), which is based on the presence of a choroidal neovascularization.

There is still no treatment for dry AMD and for most of RPs.

As such, the transplantation of RPE cells derived from human pluripotent stem cells (hPSC-RPE) represents an attractive strategy for treating retinal degenerative diseases.

hPSCs spontaneously differentiate into RPE cells after removal of basic fibroblast growth factor (bFGF), used to maintain the pluripotency state, from the culture medium. The distinctive cobblestone morphology of RPE cells as well as their pigmentation allow to manually collect pigmented areas that appear upon differentiation of hPSCs to obtain a pure population of hPSC-RPE cells. Such approach of RPE cell production is used as cell replacement material in on going and planned clinical trials. However, this spontaneous method remains fastidious, inefficient and time consuming (8 to 12 weeks of hPSCs differentiation) making it incompatible with the industrial large-scale production which is required to treat the potential millions of patients.

During the last ten years, several teams have developed improved differentiation protocols by combining the use of an increasing number of cytokines and small molecules selected on the basis of results obtained from developmental studies. One of the quickest and most efficient protocol was published in the publication "Canonical/β-catenin Wnt pathway activation improves retinal pigmented epithelium derivation from human embryonic stem cells. *Invest. Ophthalmol. Vis. Sci.* 56, 1002-1013 (2015). Following data demonstrating that RPE and neural retina progenitors (NRPs) have the same embryonic origin, they combined a protocol allowing the efficient differentiation of NRPs with previously described RPE inducing factors such as Nicotinamide, Activin A, in addition to many others including bFGF, Noggin, DKK1 (Dickkopf WNT signaling pathway inhibitor 1), Insulin Growth Factor (IGF)-1. The previous protocol was modified to include Chir99021 and SU5402 from day 8 to 14.

Using this method, they obtained cells expressing the pigmentation marker PMEL17 after 14 days of differentiation allowing bypassing manual enrichment of pigmented cells.

Background art also includes WO2017021973 and WO2008129554 which disclose two-step methods of generating retinal pigment epithelial (RPE) cells comprising culturing a population of human pluripotent stem cells in the presence of Nicotinamide; and further subjecting the cells to another stage of differentiation in the presence of activin A, with or without Nicotinamide.

Although the differentiation of hPSCs into RPE cells became more efficient during the last years, it still remains a long and laborious process requiring meticulous manipulations from hPSCs thawing to hPSCRPE cell banking. Many cell culture parameters, such as seeding homogeneity, the time spent by the cells out of the incubator or the method used to isolate pigmented clumps, could impact on the proliferation and the differentiation of hPSCs. Thus, manual processing implies operator to operator variability and the quality of hPSCs and the efficiency of their differentiation into RPE cells are currently highly dependent on technical skills. In this regard, automation should not only allow scaling up the production of hPSC-RPE cells but should also increase its robustness. It could enable larger and more reliable cell production for clinical and disease modeling applications.

Until recently, the requirement of a manual enrichment to obtain a pure population of hPSC-RPE cells prevented the use of these automated systems for the differentiation of this cell type.

Thus, a need exists for developing a fully automated process allowing a large-scale production of hPSC-RPE cells.

Considering that, in addition to considerably complicate the process, the use of numerous growth factors and small molecules on a large scale is very expensive, especially for an automated process which requires significant dead volumes, the Applicant answers this need by providing a simplified RPE differentiation protocol amenable for automation.

SUMMARY OF THE INVENTION

In accordance with a first embodiment, the present invention provides the use of a protocol amenable for automation that combines in a sequential manner three differentiating agents to direct the differentiation of hPSCs into RPE cells. This novel differentiation protocol associated with the use of cell culture robots open new possibilities for the production of large batches of hPSC-RPE cells while maintaining a high cell purity and functionality.

Thus, an object of the present invention is to provide methods for large-scale automated production of RPE cells derived from (human) pluripotent stem cells.

The hPSCs in the culture system of the methods disclosed herein are differentiating hPSCs, i.e. a population of hPSCs essentially in an undifferentiated state, or wherein at least part of said cells have been induced to undergo initial stages of directed differentiation, the majority of said cells have been induced to undergo initial stages of directed differentiation. In accordance with one embodiment, the initial stage of differentiation is achieved by exposing the cells to a first differentiating agent, in particular at least one Nicotinamide (NA) mimetic compound, then to a second differentiating agent, in particular at least one member of transforming growth factor β (TGF β) superfamily and finally to a third differentiating agent, in particular at least one activator of the Wnt canonical pathway.

DETAILED DESCRIPTION OF THE INVENTION

In the following description and claims use will be made, with a variety of terms, and the meaning of such terms as they should be construed in accordance with the present teaching is as follows:

The term "mimetic" refers to a compound having similar functional and/or structural properties to another known compound or a particular fragment of that known compound, such as a known compound of biological origin, e.g., a polypeptide or fragment thereof.

"Undifferentiated", as used herein, refers to cultured cells when a substantial proportion (at least 20%, and possibly over 50% or 80%) of the cells and their derivatives in the population display characteristic markers and morphological characteristics of undifferentiated cells, distinguishing them from differentiated cells of embryo or adult origin. Cells are recognized as proliferating in an undifferentiated state when they go through at least 1 population doubling during a cultivation period of at least 3 weeks, while retaining at least about 50%, or the same proportion of cells bearing characteristic markers or morphological characteristics of undifferentiated cells after said cultivation period.

It is intended, for the purposes of the present invention, that the term pluripotent stem cell embraces any cell having the capacity for self-renewal and the potential to differentiate into one or more other cell types.

"Pluripotent hSCs" as used herein, refer to precursor cells of human source that have the ability to form any adult cell. Such cells are true cell lines in that they: (i) are capable of extensive proliferation in vitro in an undifferentiated state; and (ii) are capable of differentiation to derivatives of all three embryonic germ layers (endoderm, mesoderm, and ectoderm) even after prolonged culture. Human embryonic stem cells (hESCs) are derived from fertilized embryos that are less than one week old (in the cleavage or blastocyte stage) or produced by artificial means (such as by nuclear transfer) that have equivalent characteristics. Other pluripotent hSCs include, without being limited thereto, multipotent adult progenitor cells (MAPs), induced pluripotent stem cells (iPS cells) and amniotic fluid stem cells.

hPSCs can be obtained using well-known cell-culture methods. For example, hESC can be isolated from single blastomeres of the cleavage or morula stage human embryo, from cleavage stage and morula human embryos and human blastocysts. Human embryos may be obtained from in vivo preimplantation embryos or more typically from in vitro fertilized (IVF) embryos. Alternatively, non-fertilized human oocyte can be parthenogenetically activated to cleave and develop to the blastocyst stage. In addition a single cell human embryo can be expanded to the blastocyst stage. For the isolation of hESCs from a blastocyst, the zona pellucida is removed and the inner cell mass (ICM) is isolated by immunosurgery, in which the trophectoderm cells are lysed and removed from the intact ICM by gentle pipetting. The ICM is then plated in a tissue culture flask containing the appropriate medium which enables its outgrowth. Following 9 to 15 days, the ICM derived outgrowth is dissociated into clumps either by mechanical dissociation or by enzymatic digestion and the cells are then re-plated on a fresh tissue culture medium. Colonies demonstrating undifferentiated morphology are individually selected by micropipette, mechanically dissociated into clumps, and re-plated. Resulting ESCs are then routinely split every 1-2 weeks. For further details on methods of preparation of hESCs; see Thomson et al. [U.S. Pat. No. 5,843,780; Science 282:1145, 1998]

In the present invention, ES cells are not limited to a primary cell line collected from the inner cell mass, but may also be an established ES cell line. Examples of such an established ES cell line include: a cell line furnished from a cell population obtained by allowing the already established ES cell line to grow; and an ES cell line obtained by thawing a freeze-dried cell line and then culturing it. Such an established ES cell line is available without going through a step of disintegrating a fertilized egg.

Otherwise, the ES cells used in the present invention may be established from a single embryonic blastomere at the cleavage stage before the blastocyst stage, without impairing the generating ability of the embryo. Such ES cells can be obtained without destroying a fertilized egg (Klimanskaya I. et al., (2006) Nature 444: 481-485; and Chung Y et al., (2008) Cell Stem Cell 2: 113-117).

Commercially available hPSCs can be also used in accordance with the invention. hPSCs can be purchased for example from the UK Stem Cell Banks or the NIH human embryonic stem cells registry. Non-limiting examples of commercially available embryonic stem cell lines are BG01, BG02, BG03, BG04, CY12, CY30, CY92, CY10, TE03 and TE32.

For ethical reasons, the present invention preferably does not pertain to objects that may be considered as contrary to"order public" or morality. Therefore, in the context of the invention, the terms "human embryonic stem cells" preferably refer to human embryonic stem cells which isolation has not involved the destruction of an embryo. In other words, the terms "human embryonic stem cells" preferably exclude human embryonic stem cells isolated by techniques that involve the destruction of an embryo.

In the context of the invention, it is to be understood that any technique that does not involve the destruction of an embryo can be used, including those that are not described herein.

Moreover, in the context of the invention, the embryos used for obtaining human embryonic stem cells are preferably embryos that cannot give rise to a human being, such as embryos destined to be discarded following in vitro fertilization (IVF) and embryos created solely for the purpose of stem cell research.

Hence, in a yet preferred embodiment, the terms "human embryonic stem cells" (hESC) preferably refer to human embryonic stem cells isolated from discarded embryos, research embryos, or preferably isolated by techniques that do not involve the destruction of an embryo.

The "induced pluripotent stem cell" in the present invention is a cell induced to have pluripotency by reprogramming a somatic cell by a known method and the like. Specifically, a cell induced to have pluripotency by reprogramming differentiated somatic cells such as fibroblast, peripheral blood mononuclear cell and the like by the expression of a combination of a plurality of genes selected from the group consisting of reprogramming genes including Oct3/4, Sox2, Klf4, Myc (c-Myc, N-Myc, L-Myc), Glis1, Nanog, Sall4, lin28, Esrrb and the like can be mentioned. Examples of preferable combination of reprogramming factors include (1) Oct3/4, Sox2, Klf4, and Myc (c-Myc or L-Myc), and (2) Oct3/4, Sox2, Klf4, Lin28 and L-Myc.

Induced pluripotent stem cell was established by Yamanaka et al. in mouse cell in 2006. In 2007, Induced pluripotent stem cell was also established from human fibroblast, and has pluripotency and self-renewal competence similar to those of embryonic stem cells.

The terms "differentiation", "differentiating" or "derivatives thereof" as used herein denote a process by which an unspecialized or relatively less specialized cell becomes relatively more specialized. In the context of cell ontogeny, the adjective "differentiated" is a relative term. Hence, a "differentiated cell" is a cell that has progressed further down a certain developmental pathway than the cell it is being compared with. A relatively more specialized cell may differ from an unspecialized or relatively less specialized cell in one or more demonstrable phenotypic characteristics, such as, for example, the presence, absence or level of expression of particular cellular components or products, e.g., RNA, proteins or other substances, activity of certain biochemical pathways, morphological appearance, proliferation capacity and/or kinetics, differentiation potential and/or response to differentiation signals, etc., wherein such characteristics signify the progression of the differentiation towards the relatively more specialized cell.

In the present context, the method of the invention results in the progressive differentiation of (human) pluripotent stem cells and differentiating cells towards RPE cells. Thus, as used herein, the term "differentiating" of differentiating cells to RPE cells may be considered synonymous to the term "obtaining" RPE cells from differentiating cells.

According to the present invention, the (human) pluripotent stem cells are subjected to directed differentiation using at least two, more preferably three differentiating agents.

"Cell marker", as used herein, refers to any phenotypic feature of a cell that can be used to characterize it or discriminate it from other cell types. A marker may be a protein (including secreted, cell surface, or internal proteins; either synthesized or taken up by the cell); a nucleic acid (such as an mRNA, or enzymatically active nucleic acid molecule) or a polysaccharide. Included are determinants of any such cell components that are detectable by antibody, lectin, probe or nucleic acid amplification reaction that are specific for the marker of the cell type of interest. The markers can also be identified by a biochemical or enzyme assay or biological response that depends on the function of the gene product. Associated with each marker is the gene that encodes the transcript, and the events that lead to marker expression. A marker is said to be preferentially expressed in an undifferentiated or differentiated cell population, if it is expressed at a level that is at least 50% higher (in terms of total gene product measured in an antibody or PCR assay) or 30% more frequently (in terms of positive cells in the population) than an acceptable control.

Whether or not the cells obtained are retinal progenitor cells or RPE cells can be determined by a method known per se, for example, the expression of a retinal progenitor cell marker. As examples of the retinal progenitor cell marker, Pax6 (neural retinal progenitor cells, retinal pigment epithelium progenitor cells), RAX (neural retinal progenitor cells), and MITF (retinal pigment epithelium progenitor cells) can be mentioned.

In one embodiment, the tissue/cell specific markers can be detected using immunological techniques. Examples include, but are not limited to, flow cytometry for membrane-bound or intracellular markers, immunohistochemistry for extracellular and intracellular markers and enzymatic immunoassay, for secreted molecular markers.

Following the stages of differentiation described herein above, a mixed cell population is obtained comprising both pigmented and non-pigmented cells.

The mature RPE cells express significantly higher levels of transcripts of markers of mature RPE cells such as MITF, PAX6 as compared to their expression in RPE cells produced by spontaneous differentiation.

The culture obtained by a method of the present invention contains RPE cells and/or the differentiating cells at high frequency (content amount). Cells obtained by a method of the present invention are PAX6, MITF-positive at high frequency, for example, at a frequency (colony frequency) of 5% or more, preferably 10 to 50%, more preferably 60 to 90%.

According to the invention, the term "differentiation" refers to the process by which a cell acquires the features of a more differentiated (or "specialized") cell.

Thus, in the context of the invention, a differentiated cell or a differentiation-induced cell is one that has more specialized features, compared to an undifferentiated cell, wherein said features correspond to a more differentiated stage within the lineage of a cell.

According to the invention, the lineage of a cell encompasses all of the discrete development stages of a cell within a scheme of development, that is to say from an undifferentiated stage to a differentiated stage. In that regard, according to the invention, a lineage-specific marker refers to a marker specifically associated with the phenotype of cells of a lineage of interest and can be used to assess the differentiated status of a cell. (FIG. 1A)

As used herein the term "sequential steps" refers to a method in which each step (e.g steps a) to c)) is performed at a different point in time, in a successive way. Unless otherwise indicated herein, as used herein "sequentially (sequential)" refers to a normal order or sequence.

As used herein, the term "Wnt signaling pathway" denotes a signaling pathway which may be divided in two pathways: the "canonical Wnt/beta catenin signaling pathway" and the "Wnt/PCP signaling pathway". As used herein, the term "canonical Wnt/beta catenin signaling pathway" or "Wnt/PCP signaling pathway" in its general meaning denotes a network of proteins and other bioactive molecules (lipids, ions, sugars . . . ) best known for their roles in embryogenesis and cancer, but also involved in normal physiological processes in adult animals. The "canonical Wnt/beta catenin signaling pathway" is characterized by a Wnt dependent inhibition of glycogen synthase kinase 3B (GSK-3B), leading to a subsequent stabilization of B-catenin, which then translocates to the nucleus to act as a transcription factor. The "Wnt/PCP signaling pathway" does not involve GSK-3 B or B-catenin, and comprises several signaling branches including Calcium dependant signaling, Planar Cell Polarity (PCP) molecules, small GTPases and C-Jun N-terminal kinases (JNK) signaling.

As used herein the term "activator" denotes a substance that enhances Wnt signaling activity.

In another embodiment, the activator of the Wnt signaling pathway is an inhibitor of GSK-3 β.

Thus, according to one embodiment, the present invention provides an automated method for promoting directed differentiation of human pluripotent stem cells into retinal pigment epithelium (RPE) cells, the method comprising or consisting in the sequential steps of:

(a) culturing human pluripotent stem cells in a medium supplemented with at least one Nicotinamide (NA) mimetic compound to generate differentiating cells;

(b) culturing said differentiating cells obtained in step a) in a medium supplemented with at least one compound of transforming growth factor β (TGF β) superfamily to further differentiating said differentiating cells;

(c) culturing said further differentiating cells obtained in step b) in a medium supplemented with at least one activator of the Wnt canonical pathway to induce said further differentiating cells to differentiate into a population of RPE cells.

The (human) pluripotent stem cells may be obtained from various culture systems in which the (human) pluripotent stem cells are maintained in an undifferentiated pluripotent state. For example, the hPSCs are cultivated in a feeder-free adherent or suspension system or on feeder cells. Commonly used feeder cells include a primary mouse embryonic fibroblast (PMEF), a mouse embryonic fibroblast (MEF), a murine fetal fibroblast (MFF) a human embryonic fibroblast (HEF), a human fibroblast obtained from the differentiation of human embryonic stem cells, a human fetal muscle cell (HFM), a human fetal skin cell (HFS), a human adult skin cell, a human foreskin fibroblast (HFF), a human cell obtained from the umbilical cord or placenta, a human adult fallopian tubal epithelial cell (HAFT) and human marrow stromal cells (hMSCs). The clusters of (human) pluripotent stem cells are obtained from an adherent cell culture by dissociation of the cells from the feeder layer or extracellular matrix to form a suspension of cells. The suspension of hPSCs comprises the free floating clusters or an essentially single cell suspension from which clusters of cells are outgrown to form the cell clusters.

In one embodiment, the step a) of the method is effected for at least 3 days, preferably for 3 to 10 days and more preferably for 7 days.

In one embodiment, the human pluripotent stem cells are cultured for 3-10 or 7 days in the presence of at least one Nicotinamide (NA) mimetic compound e.g. between 0.01-100 mM, 0.1-100 mM, 0.1-50 mM, 5-50 mM, 5-20 mM, preferably 10 mM.

According to a particular embodiment, the Nicotinamide (NA) mimetic compound is a Nicotinamide derivative or a Nicotinamide mimetic compound. The term "derivative of Nicotinamide (NA)" as used herein denotes a compound which is a chemically modified derivative of the natural NA.

Thus, the Nicotinamide of the present invention includes a substituted or non-substituted Nicotinamide. In another embodiment, the chemical modification may be a deletion or replacement of a single group, e.g. to form a thiobenzamide analog of NA, all of which being as appreciated by those versed in organic chemistry. The derivative in the context of the invention also includes the nucleoside derivative of NA (e.g. Nicotinamide adenine). A variety of derivatives of NA are described, some also in connection with an inhibitory activity of the PDE4 enzyme (WO03/068233), or as VEGF-receptor tyrosine kinase inhibitors (WO01/55114). For example, the process of preparing 4-aryl-Nicotinamide derivatives (WO05/014549). Other exemplary Nicotinamide derivatives are disclosed in WO01/55114 and EP2128244.

Nicotinamide mimetic compounds include modified forms of Nicotinamide, and chemical analogs of Nicotinamide which recapitulate the effects of Nicotinamide in the differentiation and maturation of RPE cells from pluripotent cells. Exemplary Nicotinamide mimetic compounds include benzoic acid, 3-aminobenzoic acid, and 6-aminoNicotinamide. Another class of compounds that may act as Nicotinamide mimetic compounds are inhibitors of poly(ADP-ribose) polymerase (PARP). Exemplary PARP inhibitors include 3-aminobenzamide, Iniparib (BSI 201), Olaparib (AZD-2281), Rucaparib (AG014699, PF-01367338), Veliparib (ABT-888), CEP 9722, MK 4827, and BMN-673.

In one embodiment, the Nicotinamide (NA) mimetic compound is the first differentiating agent of the present method.

In a preferred embodiment, the Nicotinamide (NA) mimetic compound is Nicotimamide.

In a preferred embodiment, the concentration of Nicotinamide is about 10 mM.

In one embodiment, the step b) of the method is effected for at least 3 days, preferably for 3 to 10 days and more preferably for 7 days.

According to one embodiment, the method comprises treating the differentiating cells obtained in step a) with at least one member of the TGF β superfamily of growth factors after the hPSCs were cultured in the presence of at least one Nicotinamide (NA) mimetic compound.

Without being bound to theory, it is believed that the at least one Nicotinamide (NA) mimetic compound acts as a differentiation inducer/promoter and that similarly, the at least one member of the TGF β superfamily act as an RPE differentiation promoting factor. In addition, while not being bound by theory, it is believed that the prior exposure of the hPSCs to the at least one Nicotinamide (NA) mimetic compound provides the differentiating cells with properties that enable their response to the RPE differentiation promoting effect of the at least one member of the, TGF β superfamily.

In one embodiment, the at least one member of transforming growth factor β (TGF β) superfamily is selected from the group consisting of the transforming growth factor-like (TGF-like) group with the TGFβ subfamily, Activin, Nodal and some growth and differentiation factors (GDF), the bone morphogenetic protein like (BMP-like) group with the BMP, GDF and anti-Mullerian hormone (AMH).

In one embodiment the transforming growth factor-β (TGFβ) superfamily growth factor is a transforming growth factor-β proteins, such as the TGFβ1, TGFβ2, and TGFβ3 subtypes, as well as homologous ligands including activin, such as activin A, activin B, and activin AB In one embodiment the transforming growth factor-β (TGFβ) superfamily growth factor is nodal, anti-mullerian hormone (AMH), some bone morphogenetic proteins (BMP), such as BMP2, BMP3, BMP4, BMP5, BM P6, and BMP7, and growth and differentiation factors (GDF).

In a preferred embodiment, the at least one member of transforming growth factor β (TGF β) superfamily is Activin A.

In one embodiment, the cells produced in step b) of the method of the present invention comprise a population of cells in which at least part or at least a majority of the human pluripotent stem cells have initiated differentiation.

With respect to the supplementation with at least one member of the TGF β superfamily of growth factors, said member is presented in soluble form or affixed or associated to a matrix or cell added to the culture system or the element may be bound or complexed to other substances.

In another embodiment, the amount of said member of the TGF β superfamily in the medium is less than 20 ng/ml, 10 ng/ml, 1 ng/ml or even less than 0.1 ng/ml.

In one embodiment the concentration of Activin A is about 10 ng/ml.

In one embodiment, the medium in step (b) is substantially or completely free of the first differentiating agent (the at least one Nicotinamide (NA) mimetic compound) used in step a) of the present method.

In one embodiment, the step c) of the method is effected for at least 20 to 50 days, preferably 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 days, more preferably 28 days.

In one embodiment, the at least one activator of the Wnt canonical pathway is a GSK-3 inhibitor selected from the group consisting of 3F8, 1-Azakenpaullone, 10Z-Humenialdisine, Alsterpaullone, AI 070722, AR-A014418, AZD1080, AZD2858, Bikinin, BIO, Cazpaullone, CT98014, CT98023, CT99021 (Chir99021), Chir98014, Dibromocantharelline, GSKJ2, HMK-32, Hymenialdesine, Indirubin, Indirubin-3'-omime, IM-12, KenpauUone, L803, L803-mts, Lithium carbonate, LY2090314, Manzamine A, Meridianin, NCS693868, NP031115, Palinurine, SB216763, SB415286, TCS21311, TC-G-24, TCS2002, TDZD-8, Tideglusib, Tricantine and TWS119.

In a preferred embodiment, the at least one activator of the Wnt canonical pathway is Chir99021.

In one embodiment the concentration of Chir99021 is about 10 ng/ml.

In one embodiment, the medium in step (c) is substantially or completely free of the first and second differentiating agents) used in steps a) and b) of the present method.

In a preferred embodiment the medium in step (c) is substantially or completely free of the at least one Nicotinamide (NA) mimetic compound and the at least one compound of transforming growth factor β (TGF β) superfamily respectively used in steps a) and b).

In one embodiment, the timing of addition of the second or the third differentiating agent to the medium is not particularly limited as long as the progressive differentiating effects can be measured or estimated by any technique known to a person skilled in the art. The presence of differentiating cells (i.e retinal progenitor cells) or RPE cells can be confirmed, for example, by detecting the presence of cells expressing RAX, PAX6, MITF or VSX2.

The skilled person is able to follow the progression of the differentiation of the cells and is able to define the appropriate moment when to add the second and third differentiating agents.

In one embodiment, the step of culturing the differentiating cells obtained in step a) produces a population of differentiating cells comprising at least 50%, 60%, or preferably 70% of differentiating cells.

In one embodiment, the step of culturing the differentiating cells obtained in step b) produces a population of differentiating cells comprising more than 50%, 60%, or preferably 70% or 80% of differentiating cells.

In one embodiment, the automated method for promoting directed differentiation of human pluripotent stem cells into retinal pigment epithelium (RPE) cells, comprises or consists in the sequential steps of:

(a) culturing human pluripotent stem cells in a medium supplemented with Nicotinamide to generate differentiating cells;

(b) culturing said differentiating cells obtained in step a) in a medium supplemented with Activin A to further differentiating said differentiating cells;

(c) culturing said further differentiating cells obtained in step b) in a medium supplemented with CHIR99021 to induce said further differentiating cells to differentiate into RPE cells.

In one embodiment, during the differentiation phase (i.e during steps a) to c)) the medium is changed every 2-3 days.

In one embodiment, the method further comprises the step of (d) treating the population of cells obtained in step c) to remove the non-pigmented cells.

Without being bound to theory, the population of cells obtained in step c) comprises RPE cells and/or differentiating cells that differentiate toward RPE cells.

The hPSC-derived RPE cells form a cohesive epithelium in culture that requires long incubation times with enzymatic dissociation reagents to trigger cell detachment for further replating and amplification. This characteristic is used to enrich the culture for RPE cells by performing a two-step enzymatic dissociation procedure comprising or consisting in a washing (first short incubation time) to remove non-RPE cells with weak adherence followed by an enzymatic treatment (second incubation) to generate a homogenous population of RPE cells.

Thus, in one preferred embodiment, the step d) of the method is a two-step dissociation procedure comprising or consisting in washing and treating the cells enzymatically.

In one embodiment, this is effected enzymatically.

In a preferred embodiment the enzymatic treatment is effected with trypsin, TrypLE Select®, trypsin-EDTA, or Accutase®.

In another embodiment, step d) may comprise combinations of mechanical, enzymatic and chemical treatment—e.g. using a cell scraper or EDTA.

The automated process of the method is presented in FIG. 3.

In manual culture methods, enzymic and non-enzymic dissociation reagents are typically removed by centrifuging before the cells are transferred to fresh culture vessels. However, in the automated methods of the invention it is preferred that the passaging does not comprise a centrifugation step. This is, in part, due to the difficulty and considerable expense of integrating a centrifuge into an automated cell culture system. An advantage is to avoid exposing the cells to the shear forces that result from centrifugation.

In one embodiment, the method further comprises the step of (e) expanding the cells obtained in step d) over at least two passages.

Expansion of the RPE cells and/or the differentiating cells that differentiate toward RPE cells can be effected on an extra cellular matrix, e.g. gelatin, collagen I, collagen IV, laminin (e.g. laminin 521), fibronectin and poly-D-lysine. For expansion, the cells may be cultured in serum-free KOM, serum comprising medium (e.g. DMEM with 4% human serum) or Nutristem medium. Under these culture conditions, after passaging under suitable conditions, the ratio of pigmented cells: non-pigmented cells increases such that a population of purified RPE cells is obtained. Such cells show the characteristic polygonal shape morphology and pigmentation of RPE cells.

The RPE cells and/or the differentiating cells that differentiate toward RPE cells can be expanded in suspension or in a monolayer. The expansion of the RPE cells in monolayer cultures can be modified to large scale expansion in bioreactors by methods well known to those versed in the art.

According to this aspect of the present invention, the differentiating cells and/or the RPE cells are removed from the culture vessel, in step d) of the method.

According to one embodiment, the expansion phase is effected for at least one week, at least 2 weeks, at least 3 weeks, at least 4 weeks, at least 5 weeks, at least 6 weeks, at least 7 weeks, at least 8 weeks, at least 9 weeks or even 10 weeks. Preferably, the expansion phase is effected for 1 week-10 weeks, more preferably 2 weeks-10 weeks, more preferably, 3 weeks-10 weeks, more preferably 4 weeks-10 weeks, or 4 weeks-8 weeks.

In a preferred embodiment, during the expansion phase, the medium is changed every 2-3 days.

The precise proportions and frequencies chosen in different embodiments will depend on the type of cells being cultured, the culture medium, the type of culture vessel, and other culture parameters, and can be readily determined by the user.

According to still another embodiment, the RPE cells and/or the differentiating cells that differentiate toward RPE cells are passaged at least 1 time during the expansion phase, at least twice during the expansion phase, at least three times during the expansion phase, at least four times during the expansion phase, at least five times during the expansion phase, or at least six times during the expansion phase.

Harvesting of the expanded population of the RPE cells and/or the differentiating cells may be effected using methods known in the art (e.g. using an enzyme such as trypsin, or chemically using EDTA).

In one embodiment passaging requires dissociation of the differentiating cells, the dissociation is conveniently carried out by adding a cell dissociation reagent to the first culture vessel. The cell dissociation reagent may be an enzymic cell dissociation reagent, such as trypsin-EDTA, or Accutase, or a non-enzymic cell dissociation reagent.

In one embodiment, the passaging includes counting the cells transferred from the first culture vessel, preferably using an automated cell counting device forming part of the robotic cell culture apparatus. Following counting, the predetermined number of cells is transferred to each of the further culture vessels.

In other embodiment, the actual number of cells transferred from the first culture vessel is not counted. Rather, the number of cells is estimated based on the size of the culture vessel and the growth characteristics of the RPE cells and/or the differentiating cells under the particular culture regime being used. Thus, the passaging can comprise calculating the number of cells transferred from the first culture vessel based on one or more of (i) the initial number of RPE cells and/or the differentiating cells in the first culture vessel, (ii) the population doubling time of the RPE cells and/or the differentiating cells, (iii) the culture area of the first culture vessel, and (iv) the culture volume or surface. It will be appreciated that the culture area of the first culture vessel is particularly relevant when calculating the number of adherent RPE cells and/or the differentiating cells obtained after a given period of culture, whereas the culture volume or surface will be particularly relevant when calculating the number of RPE cells growing in suspension Alternatively, it is an option to passage the cells so that the cells from the first culture vessel are divided between a predetermined number of further culture vessels. For example, in preferred embodiments of the invention, RPE cells and/or the differentiating cells that differentiate toward RPE cells and/or the differentiating cells are passaged with a split ratio of from 1:2 to 1:10, preferably from 1:2 to 1:5.

In further embodiments of the invention, passaging is carried out when the RPE cells and/or the differentiating cells that differentiate toward RPE cells in the first culture vessel reach a predetermined percentage confluence (or, in the case of suspension cells, a predetermined cell density). Typically, the passaging is carried out when the RPE cells and/or the differentiating cells that differentiate toward RPE cells in the first culture vessel are 50 to 100% confluent, preferably 60 to 90% confluent, more preferably 70 to 80% confluent. In a preferred embodiment, the passaging is carried out when the RPE cells and/or the differentiating cells that differentiate toward RPE cells in the first culture vessel are 90, 91, 92, 93, 94, 95, 96, 97, 98, 99 or 100% confluent.

In the automated method of the invention, it is desirable, that the percentage confluence is calculated rather than being determined prior to each passage by the operator. Thus, in preferred embodiments, the percentage confluence is calculated based on one or more of (i) the number of the RPE cells and/or the differentiating cells that differentiate toward RPE cells initially present in the culture vessel, (ii) the population doubling time of the RPE cells and/or the differentiating cells that differentiate toward RPE cells, (iii) the culture area of the first culture vessel, and (iv) the culture volume or surface. In other embodiments, confluence is recorded and/or estimated automatically.

In a preferred embodiment, the passages comprises (i) dissociating RPE cells and/or the differentiating cells that differentiate toward RPE cells in a first vessel to form a suspension; (ii) transferring the RPE cells and/or the differentiating cells that differentiate toward RPE cells to at least two further culture vessels; and (iii) culturing the RPE cells and/or the differentiating cells that differentiate toward RPE cells until the RPE cells and/or the differentiating cells that differentiate toward RPE cells are 50 to 100% confluent, wherein the passages does not comprise a centrifugation step.

Preferably the passaging is repeated until either a predetermined number of culture vessels containing the RPE cells and/or the differentiating cells that differentiate toward RPE cells or a predetermined number of the RPE cells and/or the differentiating cells that differentiate toward RPE cells has been produced. In some embodiments, the point at which the predetermined number of RPE cells has been produced will be estimated based on the growth characteristics of the RPE cells and/or the differentiating cells that differentiate toward RPE cells and the previous process steps (e.g. the number of passages). It is also possible to calculate the number of the differentiating cells or RPE cells obtained by calculating the yield per culture vessel and multiplying this value by the number of culture vessels containing the RPE cells and/or the differentiating cells that differentiate toward RPE cells that have been produced.

According to a further embodiment of the invention, the medium in which the hPSCs are differentiated is any known cell culture medium known in the art for supporting cell growth in vitro, typically, a medium comprising a defined base solution, which includes salts, sugars, amino acids and any other nutrients required for the maintenance of the cells in the culture in a viable state.

According to a preferred embodiment of the invention, the medium is not a conditioned medium. Non-limiting examples of commercially available basic media that may be utilized in accordance with the invention comprise Nutristem (without bFGF and TGFP for ESC differentiation, with bFGF and TGFp for ESC expansion), Neurobasal™, KO-DMEM, DMEM, DMEM/F12, Cellgro™ Stem Cell Growth Medium, or X-Vivo™. The basic medium may be supplemented with a variety of agents as known in the art dealing with cell cultures.

In one embodiment, the medium to be used in the present method is a serum-containing medium or serum-free medium.

In one embodiment, the medium to be used in the present method is a knock out serum replacement (KOSR) containing medium.

To avoid contamination of chemically-undefined components, a serum-free medium is preferably used in the present invention. To avoid complicated preparation, for example, a serum-free medium supplemented with an appropriate amount of a commercially available serum alternative such as KSR and so on (e.g., medium of 1:1 mixture of IMDM and F-12, which is supplemented with 10% KSR, 450 μM 1-monothioglycerol and 1× Chemically Defined Lipid Concentrate, or GMEM medium supplemented with 5%-20% KSR, NEAA, pyruvic acid, 2-mercaptoethanol) is preferably used. The amount of KSR to be added to a serum-free medium in the case of human pluripotent stem cell is generally about 1% to about 30%, preferably about 2% to about 20% (e.g., about 5%, about 10%).

In one embodiment, in step a) of the method, a DMEM medium is supplemented with 20% KSR.

In one embodiment, in step b) of the method, a DMEM medium is supplemented with 20% KSR.

In one embodiment, in step c) of the method, a DMEM medium is supplemented with 20% KSR.

In one embodiment, in step e) of the method, a DMEM medium is supplemented with 4% KSR.

According to some embodiments of the present application, steps (a), (b), (c) and (e) of the method include replacing periodically all or a portion of the culture medium. For example, all or a proportion of the culture medium can be removed from the culture vessel by pipetting or by pouring used medium to waste and fresh medium can then be added. If medium is to be removed by pipetting, the culture vessel can be positioned to assist removal of the medium.

The proportion of medium volume replaced or added will vary between different embodiments of the invention and may be 10%, 20%, 30%, 40%, 50%, 60%, 70%, 80%, 90% or 100% of the culture volume or surface.

The method of the invention can be adapted for use with any type of culture vessel, including tissue culture flasks, dishes and multi-well plates. However, it is convenient to use flasks when producing large numbers of RPE cells, as this advantageously reduces the number of processing steps required to obtain a given number of cells and thus reduces the potential for cell damage during handling.

In one embodiment, T75 or T175 tissue culture vessels are used.

In another embodiment, culture chambers (e.g. Cell-Stack®) are used.

According to one embodiment, the cells in steps a) to e) are cultured on adherent substrate under normal atmospheric oxygen conditions.

Examples of adherent substrates include but are not limited to fibronectin, laminin, polyD-lysine, collagen and gelatin.

According to a preferred embodiment of the invention, the proliferation/growth medium is free of xeno contaminants i.e. free of animal derived components such as serum, animal derived growth factors and albumin.

Following harvesting, the expanded population of the RPE cells and/or the differentiating cells may optionally be cryopreserved using methods known in the art. Examples of media suitable for cryopreservation include but are not limited to 90% Human Serum/10% DMSO, CryoStor 10%, 5% and 2%, and Stem Cell Banker.

Characterization of the Cells

In one embodiment, the differentiation of human pluripotent stem cells toward RPE cells is monitored throughout the process using an automated live-cell imaging system that resides within the controlled environment of the automated cell culture platform. This non-invasive cell imaging system provides cell confluence metrics in real-time as well as phase contrast images of processed culture vessels. Each step of the differentiation protocol is thus monitored to prevent deviations from specification limits.

In electron microscope (EM) analysis the RPE cells display morphological characteristics of mature RPE cells that are not demonstrated within RPE-like cells that were derived from spontaneously differentiating hPSC such as apical villi, tight junctions, and basal membrane. The RPE cells produced by the method of the present disclosure may be used for large scale and/or long term cultivation of such cells. To this end, the method of the invention is to be performed in bioreactors or robotic cell system suitable for large scale production of cells, and in which undifferentiated hPSCs are to be cultivated in accordance with the invention. General requirements for cultivation of cells in bioreactors are well known to those versed in the art.

The population of RPE cells generated according to the methods described herein is characterized according to a number of different parameters. For example, the RPE cells obtained are polygonal and pigmented.

It will be appreciated that the cell populations disclosed herein are devoid of undifferentiated hPSCs. According to one embodiment, less than 1:250,000 cells are Oct4+ TRA-1-60+ cells, as measured for example by FACS.

The RPE cells of this aspect of the present invention do not express pluripotent stem cell markers. Said one or more embryonic stem cell markers may comprise OCT-4, NANOG, Rex-1, alkaline phosphatase, Sox2, TDGF-beta, SSEA-3, SSEA-4, TRA-1-60, and/or TRA-1-81.

The RPE preparations may be substantially purified, with respect to non-RPE cells, comprising at least about 75%, 80%, 85%, 90%, 91%, 92%, 93%, 94%, 95%, 96%, 97%, 98%, 99%, or 100% RPE cells.

Another way of characterizing the cell populations disclosed herein is by marker expression. Thus, for example, at least 80%, 85%, 90%, 95% or 100% of the cells express Bestrophin 1, as measured by immuno staining. According to one embodiment, between 80-100% of the cells express bestrophin 1.

According to another embodiment, at least 80%, 85%, 87%, 89%, 90%, 95%, 97% or 100% of the cells express Microphthalmia-associated transcription factor (MITF), as measured by immuno staining. For example, between 80-100% of the cells express MITF.

According to another embodiment, at least 80%, 85%, 87%, 89%, 90%, 95%, 97% or 100% of the cells express both Microphthalmia-associated transcription factor (MITF) and bestrophin 1, as measured by immuno staining. For example, between 80-100% of the cells co-express MITF and bestrophin 1.

According to another embodiment, at least 50%, 60% 70% 80%, 85%, 87%, 89%, 90%, 95%, 97% or 100% of the cells express paired box gene 6 (PAX-6) as measured by immunostaining or FACS.

According to another embodiment, at least 80%, 85%, 87%, 89%, 90%, 95%, 97% or 100% of the cells express cellular retinaldehyde binding protein (CRALBP), as measured by immunostaining. For example, between 85-100% of the cells express CRALBP.

According to another embodiment, at least 80%, 85%, 87%, 89%, 90%, 95%, 97% or 100% of the cells express retinal pigment epithelium-specific protein 65 kDa (RPE65), as measured by immunostaining. For example, between 80-100% of the cells express RPE65.

The RPE cells typically co-express markers indicative of terminal differentiation, e.g. bestrophin 1, CRALBP and/or RPE65.

Following the expansion phase cell populations comprising RPE cells are obtained whereby at least 70%, 71%, 72%, 73%, 74%, 75%, 76%, 77%, 78%, 79, 80%, 81%, 82%, 83%, 84%, 85%, 86%, 87%, 88%, 89, 90%, 91%, 92%, 93%, 94%, 95%, 96%, 97%, 98%, 99 or even 100% thereof are CRALBP+, PMEL17+.

In some embodiments, the method further comprises the steps of (f) harvesting and banking the RPE cells.

Description of the Apparatus

The apparatus used to implement the method of the present invention is selected from any of a number of automated platforms for cell culture that are available and adapted for large-scale production of stem cells or differentiated cells derived from stem cells.

The Applicant has obtained good results using the CompacT SelecT® platform, manufactured by the Sartorius, but it will be understood that other systems can be adapted to provide apparatus according to the invention, which can be used to carry out the methods of the invention.

In one embodiment, the invention provides apparatus adapted or arranged for carrying out the methods of the invention. Thus, the invention provides an apparatus for large-scale automated production of cells comprising: a) robotic means for handling culture vessels; b) means for inoculating cells into a culture; c) means for changing or adding medium to a culture; and d) programmable control means; wherein the apparatus is adapted to the phase of directed differentiation of hPSCs toward RPE cells and the phase of passage the cells.

Such means are conveniently provided using an automated pipetting station, preferably using disposable pipettes, and, optionally, additional liquid pumps, thus permitting programmable medium selection and additive dispensing of different media and or reagents without risk of cross-contamination.

Thus, the apparatus may further comprise means for adding further components to a culture. In some embodiments, separate systems will be provided for adding or removing media, reagents and/or cells to and from culture vessels of different types. For example, the apparatus may comprise separate dispensing stations for tissue culture flasks and multi-well plates. Additional means may also be supplied, e.g. for adding growth factors or cell dissociation reagents.

The apparatus also includes incubators for any culture vessel format described herein, typically including at least one of an incubator for flasks and an incubator for tissue culture plates. In use, the apparatus will typically provide control of one or more of the temperature, the $CO_2$ level, the $O_2$ level and the relative humidity at which the stem cells are cultured.

The apparatus will also provide aseptic conditions to prevent contamination of cultures and ensure operator safety, suitably using a negative pressure laminar airflow hood.

In preferred embodiments the apparatus also comprises means for automated cell counting to provide consistent and accurate cell densities when seeding new culture vessels. Means for automated determination and/or estimation of percentage confluence can also be included.

The apparatus can also comprise imaging equipment or other detection means. Such means can, for example, be used to detect the expression of fluorescent reporter genes (e.g. GFP) in the cells being cultured. For example, the cells may express a reporter gene, optionally provided by means of a construct comprising an internal ribosome entry site (IRES). The percentage of reporter-positive cells can be used to determine when to passage or induce differentiation of the stem cells in a culture. Imaging equipment can also be used to assess when to harvest cells.

According to the invention, the apparatus incorporates a small six-axis anthropomorphic robotic arm that can access 90 T175 culture vessels and 210 plate incubators. The system allows the automation of seeding, feeding and other cell culture processes in order to maintain cell lines in standard T175 cell culture vessels. Culture vessels are bar-coded for identification and cell process tracking. Two culture vessels decappers and flask holders, automated medium pumping and an automatic cell counter are integrated within a high-efficiency particulate air (HEPA) filtered cabinet to ensure sterility.

In one embodiment, the CompacT SelecT® has also been shown to be successful at preventing contamination when the GMP version of the CompacT SelecT® passed the sterile fill tests.

In one embodiment, the CompacT SelecT® allows activities during cell culture such as seeding, media changes and measurement cells in a controlled environment. Thus this platform can be used to expand and differentiate batches of cells to a tighter specification than manual cell culture.

The automation enables scale out for conventional formats with predictable process variation and quality outcome by removing manual interventions. The CompacT SelecT® is a preferred platform for development process friendly method of automating the culture of cells that grow in adherent conditions.

The Cells Obtained by the Method and their Uses

The RPE cells obtained by the method of the present invention may also serve as an unlimited source of RPE cells for transplantation, replenishment and support of malfunctioning or degenerated RPE cells in retinal degenerations and other degenerative disorders. Furthermore, genetically modified RPE cells may serve as a vector to carry and express genes in the eye and retina after transplantation.

Eye conditions for which the RPE cells may serve as therapeutics include, but are not limited to retinal diseases or disorders generally associated with retinal dysfunction, retinal injury, and/or loss of retinal pigment epithelium. A non-limiting list of conditions which may be treated in accordance with the invention comprises retinitis pigmentosa, lebers congenital amaurosis, hereditary or acquired macular degeneration, age related macular degeneration (AMD), dry AMD, Best disease, retinal detachment, gyrate atrophy, choroideremia, pattern dystrophy as well as other dystrophies of the RPE, Stargardt disease, RPE and retinal damage due to damage caused by any one of photic, laser, inflammatory, infectious, radiation, neo vascular or traumatic injury.

The RPE cells generated as described herein may be transplanted to various target sites within a subject's eye or other locations (for example in the brain). In accordance with one embodiment, the transplantation of the RPE cells is to the subretinal space of the eye, which is the normal anatomical location of the RPE (between the photoreceptor outer segments and the choroid). In addition, dependent upon migratory ability and/or positive paracrine effects of the cells, transplantation into additional ocular compartments can be considered including the vitreal space, inner or outer retina, the retinal periphery and within the choroids.

The number of viable cells that may be administered to the subject are typically between 50,000-5×10$^6$ per injection.

The cells are typically formulated in a carrier (e.g. an isotonic solution and/or a saline) such as BSS Plus™. Other contemplated solutions include cryopreservation solutions such as Cryostor 5 or Cryostor 2.

The transplantation may be performed by various techniques known in the art. Methods for performing RPE transplants are described in, for example, U.S. Pat. Nos. 5,962,027, 6,045,791, and 5,941,250.

The step of administering may comprise intraocular administration of the RPE cells into an eye in need thereof. The intraocular administration may comprise injection of the RPE cells into the subretinal space.

In accordance with one embodiment, transplantation is performed via pars plana vitrectomy surgery followed by delivery of the cells through a small retinal opening into the sub-retinal space or by direct injection.

The present invention provides a pharmaceutical composition containing an effective amount of a retinal tissue or retinal cells (e.g., retinal progenitor cell, retinal layer-specific neural cell) produced by the production method of the present invention.

The pharmaceutical composition contains an effective amount of a retinal tissue or retinal cells (e.g., retinal progenitor cell, retinal layer-specific neural cell) produced by the production method of the present invention, and a pharmaceutically acceptable carrier.

Relative gene expressions were quantified by RT-qPCR and normalized to mRNA expression at day 0 (n=3, mean±SD). Control condition corresponds to RPE 20% KSR medium.

Figure 2:
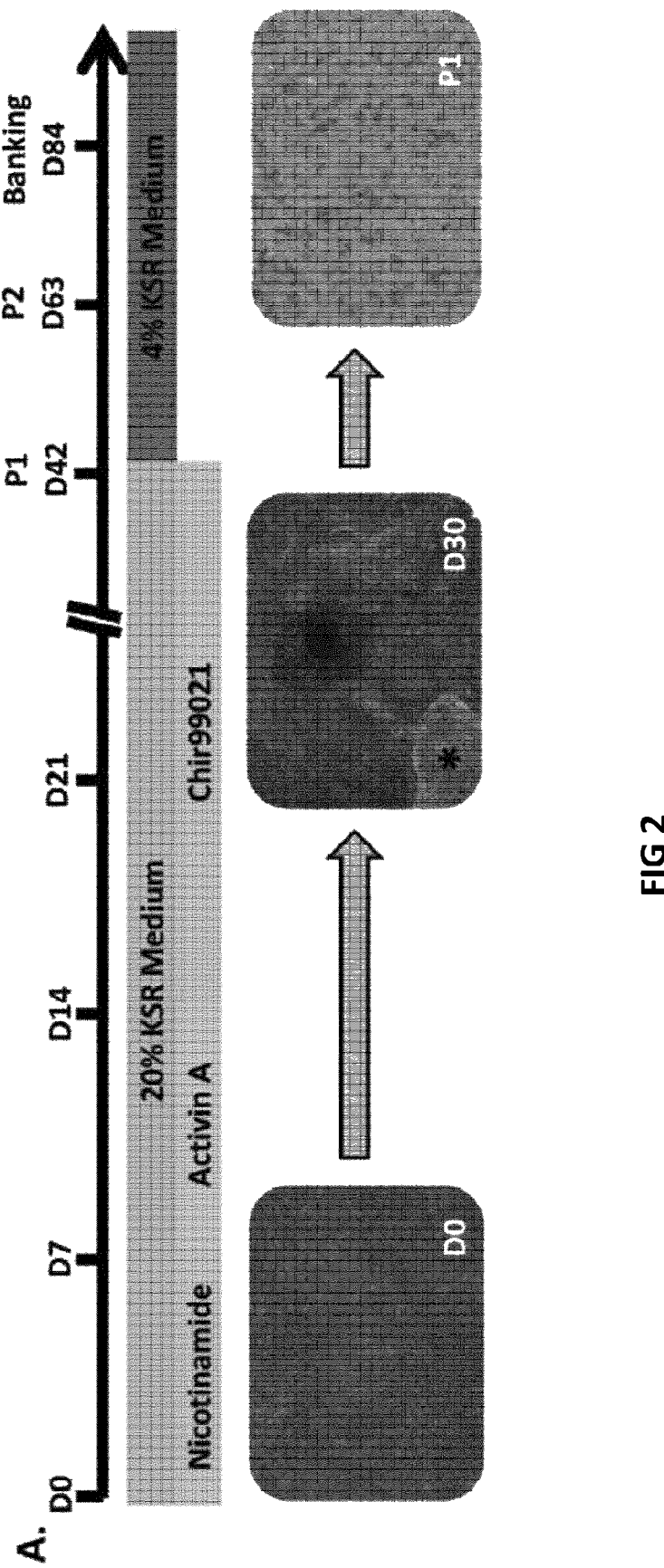

FIG. 2: Directed differentiation protocol improves RPE differentiation. (A) Schematic representation of the directed differentiation protocol (black star: cell contaminants).

Figure 3:
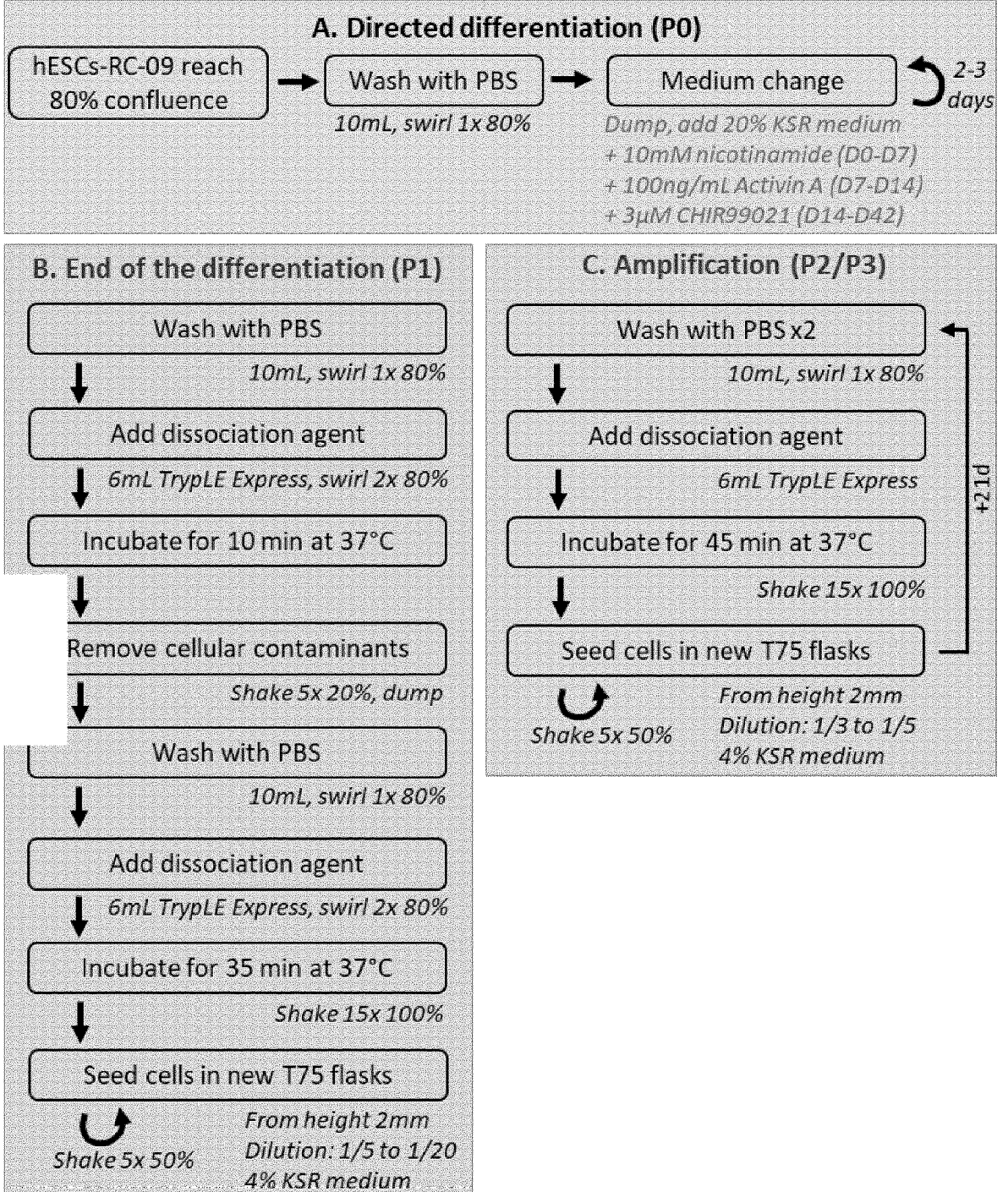

FIG. 3: Flowchart of the automated passaging of hESC-RPE cells using the Compact Select automation platform.

Figure 4:
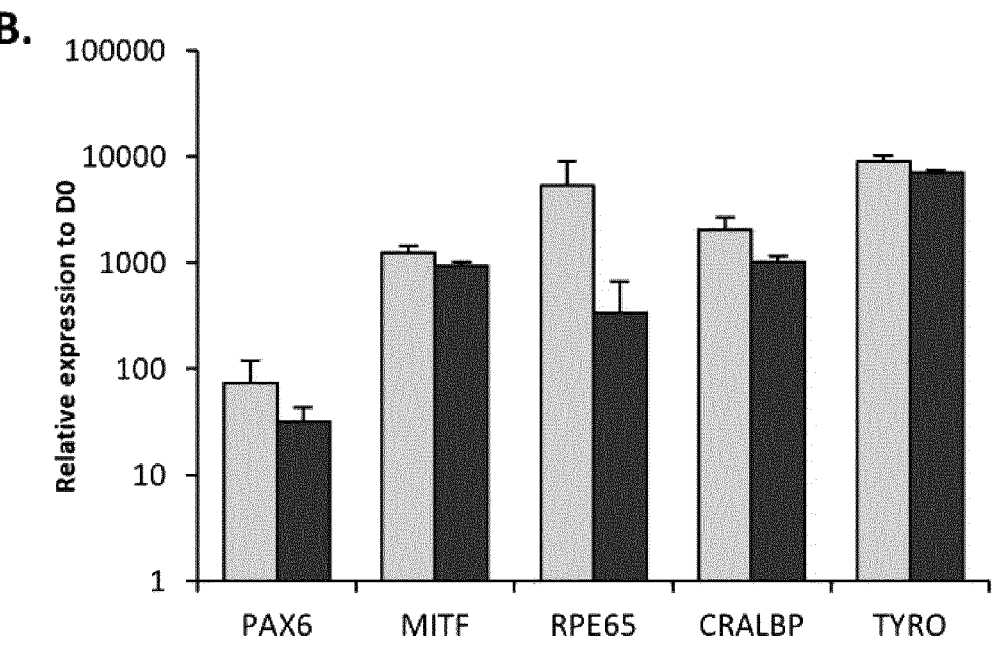
Figure 4:
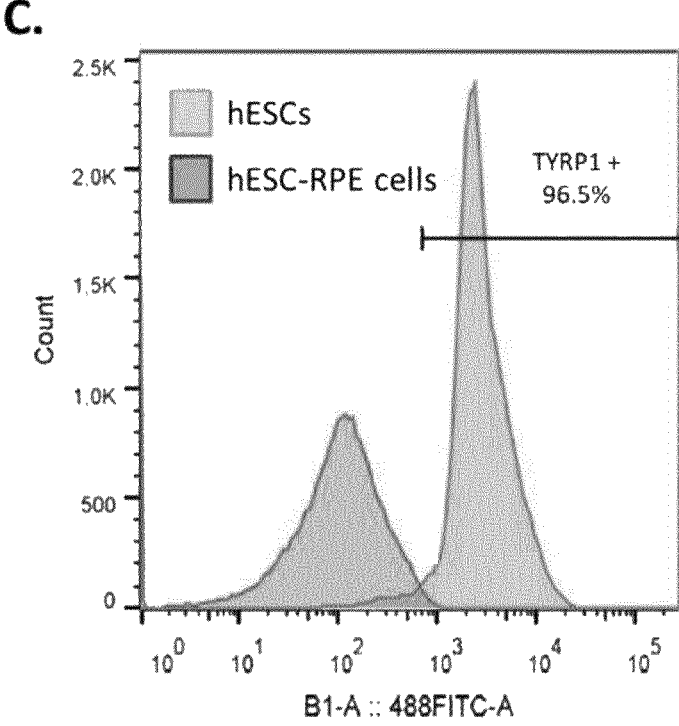

FIG. 4: Automated differentiation and amplification of a pure population of hESC-RPE cells without manual selection. (A) Representative immunofluorescence and quantification for the RPE markers MITF and PAX6 at passage 2 after 21 days of culture. Nuclei are stained with DAPI. (B) Relative gene expression of RPE markers quantified by RT-qPCR (n=3, mean±SD). (C) Representative flow cytometry histogram for the pigmentation marker TYRP1.

Figure 5:
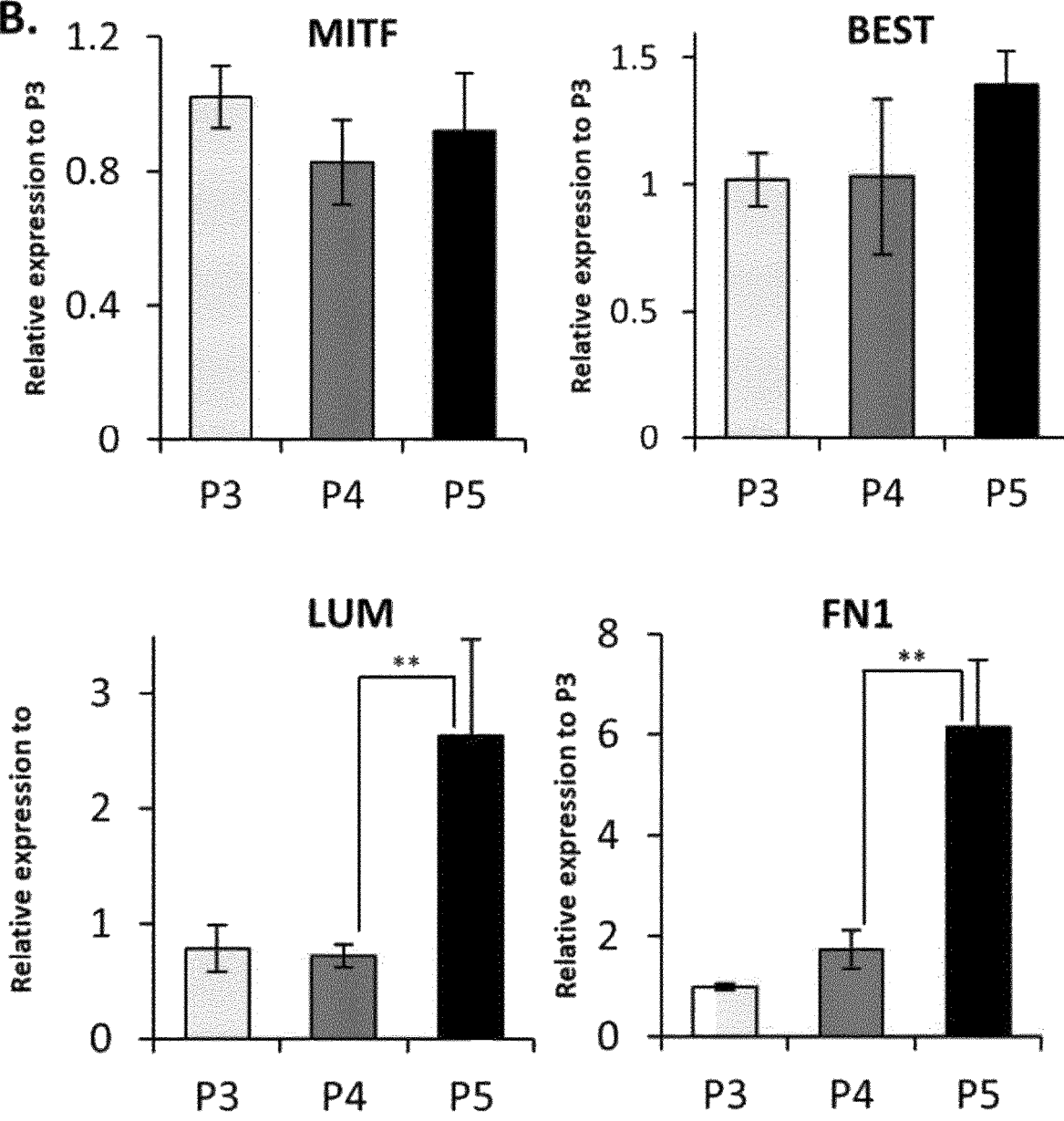

FIG. 5: hESC-RPE cells obtained by automated differentiation can be maintained in culture until passage 3 before starting an EMT. (A) Light microscopy images of hESC-RPE cells at passage 3, 4 and 5 at day 21. (B) Relative gene expression of EMT (LUM and FN1) and RPE (MITF and BEST) markers quantified by RT-qPCR (n=3, mean±SD).

Figure 6:
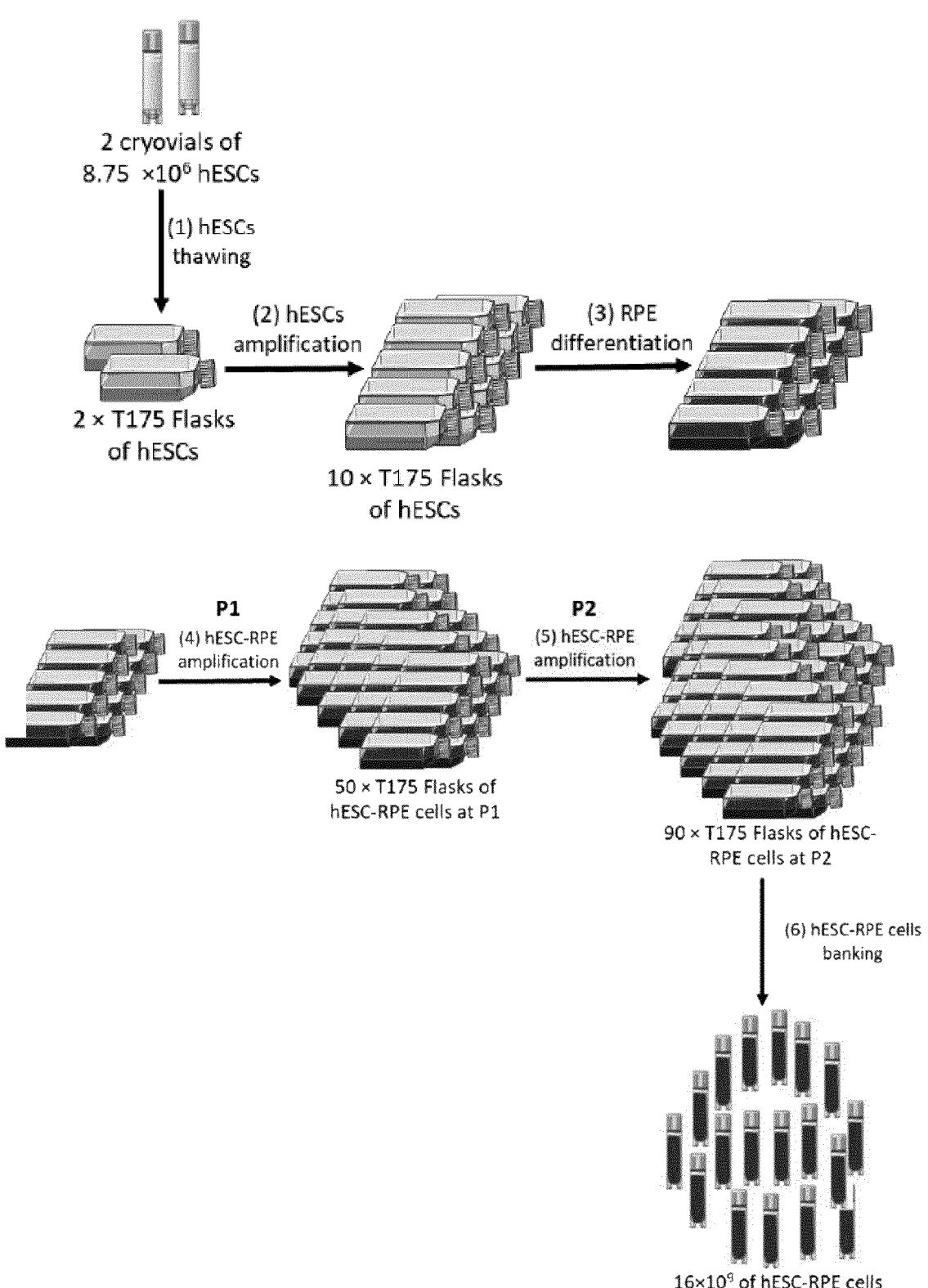

FIG. 6: Schematic representation of the automated hESC RPE cells production process. Steps 2 to 5 can be performed using the CompacT SelecT system automation platform Step 6 can be performed using automated cryovial filing system Fill it and the controlled rate freezing system Cryomed FIG. 7: Overview of the CompacT SelecT® platform: (A) Flask carousel incubator, (B) Plate incubator, (C) Media pumps, (D) Decappers, (E) Robot arm, (F) Pipette head and (G) IncuCyte live cell analysis System.

EXAMPLES

Methods

Manual hESCs Culture and RPE Cell Differentiation

Clinical-grade hESC line RC-0913, was used and cultured in feeder free conditions using mTeSR™ Medium (StemCell technologies) and hESC qualified Matrigel (Corning). Cells were banked at passage 36 and used for RPE differentiation between passage 38 and 45. Cells were plated at 5×10$^4$ cells per cm$^2$ and grown until they reached 80 percent of confluence before switching to a differentiation medium composed of Dulbecco's modified Eagle's medium (high glucose, Thermo Fisher Scientific) supplemented with 50 μM β-mercaptoethanol, 1× minimum essential medium-nonessential amino acids (Thermo Fisher Scientific) and 20% (D0-D42) or 4% (after passage 1) of knockout serum replacement (KSR, Thermo Fisher Scientific). During all the differentiation process the medium was changed every 2/3 days.

hESC-RPE cells were obtained by spontaneous differentiation of hESCs. Briefly, hESCs were grown to confluence and switched to a bFGF deprived culture medium. Pigmented patches were then dissected under a stereomicroscope with a fine 15 ophthalmic knife and plated onto culture dishes coated with hESC qualified Matrigel (corning).

For the referred "directed differentiation" protocol, 10 mM Nicotinamide (Sigma), 100 ng/ml Activin A (Peprotech) and 3 μM CHIR99021 (Tocris) were added sequentially to the basal differentiation medium at specific time points (FIG. 2A).

Characterization of Differentiated RPEs

Quantitative Real-Time Polymerase Chain Reaction

Total RNAs were extracted using RNAeasy Plus Mini kit (Qiagen) and cDNA synthesized using SuperScript III (Invitrogen). Quantitative real-time RT-PCR was performed using a Quant Studio 12K flex (Applied Biosystems) with HiGreen qPCR Master Mix (Thermo Fisher Scientific). Primer sequences are listed in Table 1. Experiments were performed with at least three technical replicates per plate and expression levels were normalized to 18S. Relative expression compared to hESCs gene expression levels were determined by calculating the 2-ΔΔCt.

TABLE 1

List of quantitative reverse transcriptase poly-
merase chain reaction (qRT PCR) primers.

| Gene | | SEQUENCE |
|------|------|----------|
| 18S | FRW | GAGGATGAGGTGGAACGTGT |
| | REV | TCTTCAGTCGCTCCAGGTCT |
| NANOG | FRW | CAAAGGCAAACAACCCACTT |
| | REV | TCTGCTGGAGGCTGAGGTAT |
| RAX | FRW | GGCAAGGTCAACCTACCAGAG |
| | REV | CATGGAGGACACTTCCAGCTT |
| SIX3 | FRW | CCTCCCACTTCTTGTTGCCA |
| | REV | CGCTACTCGCCAGAAGTATGG |
| PAX6 | FRW | GCCAGCAACACACCTAGTCA |
| | REV | TGTGAGGGCTGTGTCTGTTC |
| VSX2 | FRW | CTGCCGGAAGCAGGATACA |
| | REV | TAGAGCCCATACTCCGCCA |
| MITF | FRW | CCGGGTGCAGAATTGTAACT |
| | REV | GGACAATTTTGGCATTTTGG |
| RPE65 | FRW | AGCACTGAGTTGAGCAAGCA |
| | REV | GGCCTGTCTCACAGAGGAAG |
| CRALBP | FRW | CACGCTGCCCAAGTATGATG |
| | REV | CCAGGACAGTTGAGGAGAGG |

TABLE 1-continued

List of quantitative reverse transcriptase poly-
merase chain reaction (qRT PCR) primers.

| Gene | | SEQUENCE |
|------|------|----------|
| TYROSYNASE | FRW | GTGTAGCCTTCTTCCAACTCAG |
| | REV | GTTCCTCATTACCAAATAGCATCC |
| BEST1 | FRW | GTCAGAGGCTCCTCCTTCCT |
| | REV | TCTGCTCCACCAGTGTTCTG |
| LUM | FRW | CTTCAATCAGATAGCCAGACTGC |
| | REV | AGCCAGTTCGTTGTGAGATAAAC |
| FN1 | FRW | GGAAAGTGTCCCTATCTCTGATACC |
| | REV | AATGTTGGTGAATCGCAGGT |

Immunostaining hESC-RPE cells were grown on Matrigel-coated 96 or 24-well plates. Adherent cells were fixed in 4% PFA for 10 min at room temperature (RT) and rinsed 3 times with PBS. After 30 min in blocking solution (10% FBS in 0.1% Triton PBS) at RT, cells were incubated with primary antibodies overnight at 4° C. (Antibodies are listed in Table 2). After 3 washes in PBS, appropriate Alexa Fluor-conjugated secondary antibodies (Invitrogen) were added at 1:500 for 1 h at RT in presence of DAPI (Invitrogen).

TABLE 2

List of primary antibodies.

| Antibody | Host | Company | Reference | Dilution | Application |
|----------|------|---------|-----------|----------|-------------|
| PAX6 | Rabbit | Biolegend | PRB-278P | 1/500 | Immunofluorescence |
| MITF | Mouse | Dako | M3621 | 1/250 | Immunofluorescence |
| VSX2 | Goat | Santa Cruz Biotechnology | sc-21690 | 1/250 | Immunofluorescence |
| TYRP1 | Mouse | LifeSpan BioSciences | MS-771-P1 | 1/500-1/100 | Flow cytometry |
| EZRIN | Mouse | Sigma | E8897 | 1/250 | Immunofluorescence |
| ZO-1 | Rabbit | Invitrogen | 402300 | 1/500 | Immunofluorescence |
| BEST | Mouse | Abcam | ab2182 | 1/250 | Immunofluorescence |
| MERTK | Rabbit | Abcam | Y323 | 1/500 | Immunofluorescence |
| NANOG | Rabbit | Abcam | ab80892 | 1/500 | Immunofluorescence |
| OCT 3/4 | Goat | Santa Cruz Biotechnology | sc-5279 | 1/500 | Immunofluorescence |
| SSEA4 | Mouse | R&D systems | FAB1435A | 1/100 | Flow cytometry |
| TRA1-60 | Mouse | Santa Cruz Biotechnology | sc-21705 | 1/500 | Immunofluorescence |
| TRA1-81 | Mouse | Santa Cruz Biotechnology | sc-21706 | 1/500 | Immunofluorescence |
| TRA1-81 | Mouse | eBioscience | 12-8883-82 | 1/100 | Flow cytometry |

Image Acquisition and Analysis

Images were acquired with an Axio observer Z1 microscope (Zeiss) with a Hamamatsu ORCA-flash 4.0 camera and a spinning disk unit (Yokogawa CSU-X1-A1N-E; Camera evolve, EMCCD 512) with Metamorph software or with a LSM-800 confocal microscope (Zeiss) with Zen software. Images were exported, analyzed and processed with Fiji software. For zx images, xy stacks (0.33 μm z step size) covering cell width were resliced in zx. The quantification of pigmented areas was performed after manual delimitation of culture dish areas using Fiji software. Pictures were then binarized to 8-bit images using a fixed intensity threshold and the black area fraction was measured (not herein shown).

Flow Cytometry

Cells were detached from culture plates, fixed in 4% PFA for 10 min at RT and permeabilized with PBS containing 0.1% Triton for 30 min before labeling with TYRP1 antibody for 1 hr at RT. Labeling of the cell surface markers TRA-1-81 and SSEA4 was performed on freshly dissociated cells for 15 min at 4° C. Cells were then incubated with fluorochrome-conjugated primary antibody for 30 min at RT and rinsed twice with PBS. The antibodies used and their working dilutions are listed in Supplementary Table 2. Cells were analyzed using a cell MACSquant analyzer (MiltenyiBiotec). Gates were drawn according to fluorescence minus one (FMO) controls or on samples labeled with isotype control antibodies. Data were analyzed using Flowio software (Tree Star, Ashland, OR).

Phagocytosis Assay hESC-RPE cells were exposed for 24 hours to purified FITC-labeled photoreceptor outer segments of pig (gift from Dr. E. Nandrot). After washing with PBS, cells were fixed in cold methanol and labelled with DAPI. Images were taken with LSM-800 confocal microscope (Zeiss). hESCs derived RPE cells were also exposed to pHrodo Green Zymosan Bioparticles (Thermo Fisher Scientific) overnight at 37° C. These particles are pH-sensitive and become fluorescent after cell entry and phagosome formation. As a negative control, phagocytosis assays were performed at 4° C. to block the phagocytic process. Plates were then read using a microplate reader (Clariostar-BMG LABTECH) and values were normalized to DAPI intensities.

VEGF Quantification by ELISA Assay

VEGF measurements were done in triplicate using the human VEGF Quantikine ELISA kit (R&D System) according to manufacturer instruction.

Statistical Analysis

All experiments were performed in triplicate. Summary statistical analyses were performed in XLSTAT software. Comparisons between experiments were performed using the unpaired t-test and statistical significance was established as *p<0.05, **p<0.01.

Results

Sequential Use of Nicotinamide, Activin a and Chir99021 Improves RPE Differentiation by Recapitulating the Main Steps of Retinal Development In an effort to simplify previous directed differentiation protocols for automation, it was evaluated whether the simple use of Nicotinamide, Activin A and Chir99021 in a sequential manner (referred as "directed protocol") improves RPE cell differentiation of adherent hESCs enough to bypass manual enrichment. The efficiency of the "directed protocol" was compared with the one of the classical spontaneous differentiation.

Figure 1:
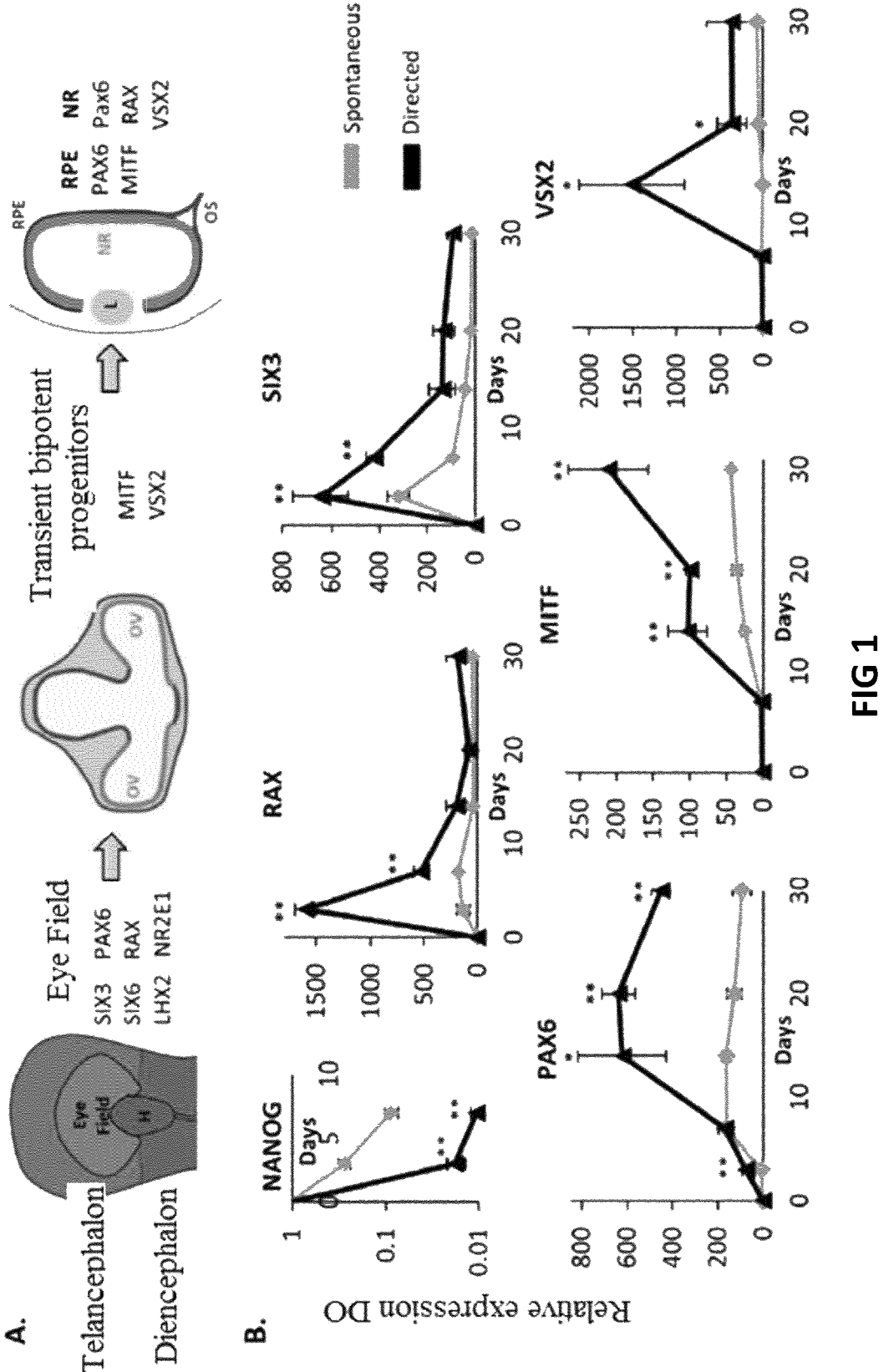
FIG. 1: (A) Schematic representation of the retinal development. H, Hypothalamus; OV, Optic Vesicle; L, Lens; NR, Neural Retina; RPE, Retinal Pigment Epithelium; OS, Optic Stalk. (B) Real-Time PCR, analyzing the expression of RPE markers in the presence of NA.

It was checked whether the sequential use of NIC, Activin A and Chir99021 could recapitulate the main steps of retinal development by evaluating the expression of markers of the early eye field stage, optic vesicle stage and immature RPE cells at different time points during the differentiation (FIG. 1A). The use of Nicotinamide for the first 7 days of differentiation significantly enhanced the transient expression of the early eye field transcription factors SIX homeobox 3 (SIX3) and Retinal homeobox (RAX) concomitantly to a higher decrease of the expression of the pluripotency marker NANOG at mRNA level when compared to the spontaneous protocol (p<0.01; FIG. 1B). This eye field specification was confirmed at the protein level with the co-expression of the LIM homeobox 2 (LHX2) and the Paired box 6 (PAX6) proteins by most cells at day 7 after Nicotinamide treatment (86.8%±4.3%, n=3), while only 44.3% (±2.2%, n=3) of the non-treated cells express these two markers. Overall, these data suggested that the addition of Nicotinamide for 7 days promotes the exit of hESCs from their pluripotent state toward the eye field lineage with a better efficiency than the spontaneous differentiation.

Consecutive treatment with Activin A from day 7 to day 14 significantly increased the expression at mRNA levels of two transcription factors involved in optic vesicle patterning, the visual system homeobox 2 gene (VSX2, also named CHX10) and the melanocyte inducing transcription factor (MITF), when compared to the spontaneous differentiation (FIG. 1B, p≤0.05), with an expression peak at day 14 for VSX2. Concomitantly, both RAX and SIX3 mRNA levels were found decreased. Induction of the optic vesicle markers VSX2 and MITF was confirmed by immunofluorescence assays. Cell clusters co-expressing these two proteins were observed by day 10. By contrast on day 14, cells expressing VSX2 were distinct from those expressing MITF, suggesting rapid co-repression of these two genes.

Finally, activation of the canonical WNT signaling pathway by CHIR99021 treatment from day 14 to day 35-42 induced RPE commitment as seen by the acute decreased expression of VSX2 mRNA levels (FIG. 1B) and the continuous increased expression of MITF. MITF expression is significantly upregulated between day 14 and day 30 in the directed protocol when compared to the spontaneous one (p<0.01). Immunostaining assays confirmed the absence of VSX2 positive cells at day 21 and the increased number of MITF+ cells (87.5%±12.5%). At this stage putative RPE precursors MITF-positive cells emerged and organized around 3D structures that did not express MITF and VSX2.

The efficiency of RPE cell induction after 6 weeks of differentiation was determined. A large majority of the culture dish with cells exposed to the directed protocol (72.96%±1.94% of the culture area, n=3) was covered by pigmented cells on day 42. By contrast, only isolated patches of pigmentation were visible with the spontaneous protocol (3.481%±1.12% of the growth area, p<0.01). Importantly, the vast majority of cells obtained after 42 days of differentiation with the directed protocol co-expressed PAX6 and MITF (82.2%%±3.2%, n=3), two markers of RPE cells.

Taken together these results indicate that the sequential use of Nicotinamide, Activin A and Chir99021 recapitulates the main steps of retinal development and efficiently directs the differentiation of hPSCs into a highly-enriched RPE population within 42 days compared to the spontaneous differentiation. Thus, cell differentiated through the directed protocol could be amplified directly while a prior manual selection of RPE clusters is required for the spontaneous protocol.

On day 42, cells were incubated with TrypLE Reagent (Thermo Fisher Scientific) for 10 minutes to remove cell contaminants, then washed with PBS and re-incubated with TrypLE Reagent for 35 minutes to allow RPE dissociation. Cells were then seeded at a final dilution of ⅕ in dishes coated with hESC qualified Matrigel (Corning).

Mature hESC-RPE cells were dissociated and cryopreserved in liquid nitrogen vapors with CryoStor CS10 medium (StemCell technologies) at passage 1 or 2.

Automated RPE Differentiation Process

Figure 7:
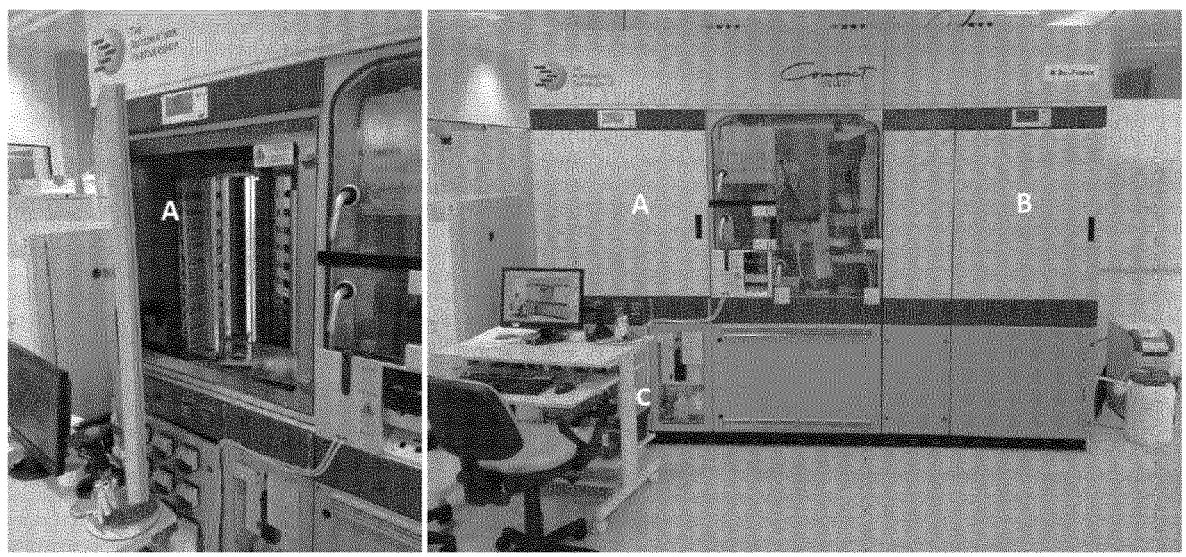
Figure 7:
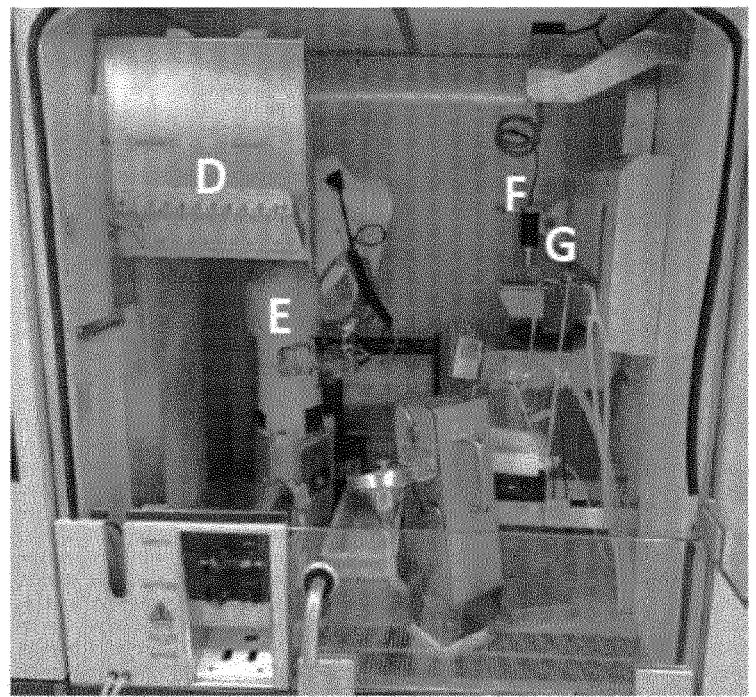

The CompacT SelecT® (Sartorius) is a fully automated cell culture platform which allows the expansion and differentiation of large batches of adherent cells in a controlled environment (FIG. 7). The system allows the automation of media changes and cell passaging as well as the monitoring of culture vessels with the automated live-cell imaging system IncuCyte (Sartorius). Contrary to the manual protocol, cells were not centrifuged after dissociation but were directly seeded into new flasks with enough medium to ensure that the final concentration of TryPLE® reagent in the daughter flasks did not exceed 5%. The automated process is presented in FIG. 3.

The directed protocol allows obtaining a pure population of hESC-RPE cells without manual enrichment and is amenable to automation of the differentiation.

Using the "directed differentiation" protocol, a fully automated process was setted up by performing media changes and enzymatic passaging using the CompacT SelecT® automation platform. This automated cell culture platform is composed of an incubator, bar-coded flasks for cell process tracking, multiple connected pumps to dispense culture media, a six-axis anthropomorphic robotic arm and a live-cell imaging system (Incucyte) (FIG. 3 and FIG. 7).

Automation starts from the seeding of hPSCs onto 75 cm2 flasks. Then, cell proliferation and differentiation initiation by medium switching were performed in the robot until day 42. At this stage, hESC-RPE cells form a cohesive epithelium in culture that requires long incubation times with dissociation reagents to trigger cell detachment for further replating and amplification. In order to eliminate a maximum of cell contaminants it was taken advantage of this characteristic by performing a differential dissociation treatment with TrypLE® (FIG. 3).

One was able to remove the vast majority of unpigmented cells that have lower adherence to the flask than RPE cells on day 42 by applying a first short incubation of 10 minutes with TrypLE® Express followed by a rinse.

A second enzyme incubation of 35 minutes then enabled the detachment and dissociation of RPE cells.

As the automated system does not include any centrifuge, it was not possible to eliminate the TrypLE used to dissociate RPE cells. Thus, it was assessed if the final 5% of TrypLE® remaining in the medium after passaging did not affect the re-adherence and the growth of the cells. No difference between cells replated in presence of 5% of TrypLE® or after a centrifugation step was observed (data not shown). It was also checked that the presence of diluted TrypLE® did not affect RPE identity and once again no difference was detected in RPE gene expression between enzymatic passaging with or without centrifugation (data not shown).

After 2 automatized passages, 94.7%±0.2% (n=3) of cells co-expressed the two transcription factors PAX6 and MITF indicating a homogenous population of hESC-RPE cells comparable with the one obtained after manual enrichment13. The gene expression of late RPE markers such as RPE65 and CRALBP was also detected by RTqPCR at a level similar to the cells obtained with the manual spontaneous differentiation protocol (FIG. 4B). The cell population was further characterized by flow cytometry and found that 96.8%±1.9 (n=3) of the cells expressed the pigmentation marker tyrosinase related protein 1 (TYRP1) at passage 2 (FIG. 4C).

All together these data demonstrate that we were able to obtain pure bona fide hESC-RPE cells in an automated system with a quality similar to the cells obtained through the widely used spontaneous differentiation method.

hESC-RPE cells obtained by an automated differentiation are mature and functional.

Important issues concerning cells differentiated from hPSCs are their maturity and functionality. As an indicator of epithelial maturity, the apico-basal polarization of specific RPE markers was evaluated. As expected, hESC-RPE cells homogeneously expressed the microvilli protein EZRIN (95.0%±2.8%, n=3), the tight junction marker Zonula Occludens-1 (ZO-1, 99.3%±0.4%, n=3) and the MER proto-oncogene tyrosine kinase receptor (MERTK, 97.1%±1.1%, n=3) at their apical membrane while the calcium activated chloride channel, BESTROPHIN (BEST, 89.4%±3.9%, n=3) was localized at the baso-lateral compartment.

One of the most important functions of RPE cells is the phagocytosis of the outer segments shed by the photoreceptors. To determine whether the cells differentiated according to this directed protocol on the automated cell culture platform were functional, we assessed their ability to phagocyte pig fluorescein isothiocyanate (FITC)—labeled photoreceptor outer segments and quantified the fluorescence signal of pH sensitive particles that become fluorescent after cell entry and phagosome formation. hESC-RPE cells were able to phagocyte FITC-labeled photoreceptor outer segments as shown by the cytoplasmic localization of the FITC signal under the apical limit Ezrin positive. hESC-RPE cells incubated with pH-sensitive particles at 37° C. had a fluorescence intensity 22.2 fold higher compared to cells incubated at 4° C., a temperature that inhibits the phagocytic process. Another indicator of RPE functionality is the ability to secrete a wide range of growth factors including the vascular endothelial growth factor (VEGF). The secretion of VEGF was quantified after several culture weeks and a progressive increased of VEGF secretion starting from 2 weeks of culture was observed.

All these results indicate that RPE cells differentiated from hPSCs using a fully automated protocol are functional in vitro. hESC-RPE cells differentiated through automation can be amplified until passage 3 to produce large cell banks.

Previous studies showed that hESC-RPE cells had a limited amplification potential before they undergo an epithelial-mesenchymal transition (EMT). In line with these studies, hESC-RPE cells obtained with an automated process adopted a mesenchymal phenotype starting from passage 4 despite the maintenance of the gene expression of the RPE markers MITF and BEST (FIG. 5B). Indeed, the cells switched from a classical cobblestone organization to elongated cell morphology. This microscopic observation is correlated with the rising expression of mesenchymal markers LUMICAN (LUM) and FIBRONECTIN 1 (FN1), two extracellular matrix proteins, starting at passage 5 when compared to passage 3 and 4 (p<0.01; FIG. 5B).

This suggests an EMT transition of hESC-RPE cells, which however maintain an RPE identity. Consequently, it was decided to bank these cells at passage 2 using an automated cell banking system (Fill-it, Sartorius) to obtain bona fide hESC-RPE cells at passage 3 after thawing.

CONCLUSION

It was demonstrated in this application that most of these cytokines and supplements were not essential to trigger an efficient and pure RPE cell differentiation. Indeed, the use of only 3 compounds (Nicotinamide, Activin A and CHIR99021) in a sequential manner allowed obtaining a pure population of RPE cells without 3-dimensional culture and manual dissection of pigmented foci during the differentiation process. This optimized differentiation is thus amenable to automation.

Using the automated differentiation process described in this application, it is possible to produce about 16 billion of hESC-RPE cells at passage 2 per batch. A bank of this size is much larger than those previously described that range from 0.05 to $0.8 \times 10^9$ cells, and could be produced by a single operator supervising the robot. Moreover, the use of HYPERflask® (Corning) with a growth area of 1720 cm$^2$ (compared to 75 cm2 flask used in this study) could even dramatically increase the number of cells produced per batch. Another way to increase the size of the bank would be to delay the EMT. Indeed, the number of passages without EMT might be extended as previously described by the addition of a ROCK inhibitor in the culture medium.

hPSC-RPE cells have been already grafted in AMD patients either as a cell suspension or a polarized epithelium resting on a synthetic basement membrane. The use of cell suspension formulation considerably simplifies the logistical and surgical procedures but several studies made in animal models, suggest that the survival of the RPE cells and the visual benefits for the animal are improved when the cells are grafted as an epithelial tissue rather than a cell suspension. In human, these two approaches have shown both satisfactory safety results and promising efficacy results, even if the extent and the causes of visual improvement in transplant recipients remain ambiguous. Nevertheless, considering that $1 \times 10^5$ hESC-RPE cells are currently used to graft a human eye with the both methods, the automated process presented here should allow to produce enough cells to treat several thousands of patients with retinal degeneration even if some steps of the production, such as the simultaneous banking of a huge numbers of cryovials, remains challenging.

In conclusion, following the previously published amplification of hPSCs using CompacT SelecT® automate, a fully automated RPE cell differentiation process from the hPSCs thawing to the banking of differentiated cells was described. Such automated process is a step towards the scale up and the industrialization of RPE differentiation that will be necessary to treat large numbers of patients. Finally, any differentiation protocol that doesn't require 3D culture or manual selection could theoretically be adapted to this automated culture system opening new perspectives concerning the scale up and the industrialization of the production of many cell types differentiated from hPSCs This protocol recapitulates the main steps of retinal development and is sufficient to obtain a pure population of RPE cells without manual enrichment. A culture robot was programmed to automate this protocol in order to upscale the production process. 16 billion of mature and functional RPE cells could now be produced within 12 weeks with only one round of production. Such efficient and reproducible automated protocol should be useful for the treatment of the millions of patients affected by RPE associated retinal degeneration. The automated culture system for preparing RPE cells is expected to be qualified for clinical cell productions in accordance with Good Manufacturing Practices (GMP) (e.g., the preparations are GMP-compliant) and/or current Good Tissue Practices (GTP) (e.g., the preparations may be GTP-compliant).

---

The invention claimed is:

1. An automated method for large-scale production of retinal pigment epithelium (RPE) cells and for promoting directed differentiation of human pluripotent stem cells into retinal pigment epithelium (RPE) cells, wherein the method comprises the use of only three differentiating agents to direct the differentiation of human pluripotent stem cells into RPE cells in the sequential steps of:

(a) culturing human pluripotent stem cells in a medium supplemented with a first differentiating agent consisting of one Nicotinamide (NA) mimetic compound to generate differentiating cells, for at least 3 days;

(b) culturing said differentiating cells obtained in step a) in a medium supplemented with a second differentiating agent, consisting of one member of transforming growth factor β (TGF β) superfamily to further differentiating said differentiating cells, for at least 3 days;

(c) culturing said further differentiating cells obtained in step b) in a medium supplemented with a third differentiating agent, consisting of one activator of the Wnt canonical pathway to induce said further differentiating cells to differentiate into RPE cells, for 20 to 50 days, wherein the Nicotinamide (NA) mimetic compound is Nicotimamide, wherein the one member of transforming growth factor β (TGF β) superfamily is selected from the group consisting of the TGFβ subfamily, Activin, Nodal, growth and differentiation factors (GDF), bone morphogenetic protein (BMP), and antiMullerian hormone (AMH), wherein the one activator of the Wnt canonical pathway is a GSK-3 inhibitor selected from the group consisting of 3F8, 1-Azakenpaullone, 10Z-Humenialdisine, Alsterpaullone, A-1070722, AR-A014418, AZD1080, AZD2858, Bikinin, BIO, Cazpaullone, CT98014, CT98023, CT99021 (Chir99021), Chir98014, Dibromocantharelline, GSKJ2, HMK-32, Hymenialdesine, Indirubin, Indirubin-3'-oxime, IM-12, Kenpaullone, L803, L803-mts, Lithium carbonate, LY2090314, Manzamine A, Meridianin, NSC693868, NP031115, Palinurine, SB216763, SB415286, TCS21311, TC-G-24, TCS2002, TDZD-8, Tideglusib, Tricantine and TWS119, and wherein the automated method uses an apparatus for large-scale production of cells comprising: a) robotic means for handling culture vessels; b) means for inoculating cells into a culture; c) means for changing or adding medium to a culture; and d) programmable control means.

2. The automated method of claim 1, wherein the medium in step (b) is free of the Nicotinamide (NA) used in step a).

3. The automated method of claim 1, wherein the medium in step (c) is free of the Nicotinamide (NA) and the one member of transforming growth factor β (TGF β) superfamily respectively used in steps a) and b).

4. The automated method of claim 1, wherein the method comprises the sequential steps of:

(a) culturing human pluripotent stem cells in a medium supplemented with Nicotinamide to generate differentiating cells;

(b) culturing said differentiating cells obtained in step a) in a medium supplemented with Activin A to further differentiating said differentiating cells;

(c) culturing said further differentiating cells obtained in step b) in a medium supplemented with CHIR99021 to induce said further differentiating cells to differentiate into RPE cells.

5. The automated method of claim 1, wherein the method further comprises the step of:

(d) treating the population of cells obtained in step c) to remove the non-adherent cells.

6. The automated method of claim 5, wherein the step d) is a two-step dissociation procedure comprising or consisting of washing and treating the cells enzymatically.

7. The automated method of claim 1, wherein the method further comprises the step of (e) expanding the cells obtained in step d) over at least two passages.

8. The automated method of claim 7, wherein the passages comprises (i) dissociating the RPE cells and/or the differentiating cells in a first vessel to form a suspension; (ii) transferring the RPE cells and/or the differentiating cells to at least two further culture vessels; and (iii) culturing the RPE cells and/or the differentiating cells until the RPE cells and/or the differentiating cells are 50 to 100% confluent, wherein the passages does not comprise a centrifugation step.

9. The automated method of claim 1, wherein the method uses a) robotic means for handling culture vessels; b) means for inoculating cells into a culture; c) means for changing or adding medium to a culture; and d) programmable control means; wherein the apparatus is adapted to the phase of directed differentiation of hPSCs toward RPE cells and the phase of passage the cells when they reach a predetermined percentage confluence.

10. The automated method of claim 1, wherein culturing said human pluripotent stem cells in a medium supplemented with Nicotinamide (NA) is carried out for 7 days.

11. The automated method of claim 1, wherein culturing said differentiating cells obtained in step a) in a medium supplemented with the one member of transforming growth factor β (TGF β) superfamily is carried out for 3 to 10 days.

12. The automated method of claim 1, wherein culturing said differentiating cells obtained in step a) in a medium supplemented with the one member of transforming growth factor β (TGF β) superfamily is carried out for 7 days.

13. The automated method of claim 1, wherein culturing said human pluripotent stem cells in a medium supplemented with Nicotinamide (NA) is carried out for 7 days, wherein culturing said differentiating cells obtained in step a) in a medium supplemented with Activin A is carried out for 7 days, wherein culturing said differentiating cells obtained in step b) in a medium supplemented with Chir99021 is carried out for 21-28 days.

14. The automated method of claim 1, wherein the method comprises the sequential steps of:

(a) culturing human pluripotent stem cells in a medium supplemented with Nicotinamide is carried out for 7 days, wherein the amount of Nicotinamide is 10 mM, (b) culturing said differentiating cells obtained in step a) in a medium supplemented with Activin A is carried out for 7 days, wherein the amount of Activin A is 10 ng/ml, (c) culturing said further differentiating cells obtained in step b) in a medium supplemented with CHIR99021 is carried out for 21-28 days, wherein the amount of Chir99021 is 10 ng/ml.

* * * * *